(12) United States Patent
Kadler et al.

(10) Patent No.: US 7,741,279 B2
(45) Date of Patent: Jun. 22, 2010

(54) MODIFIED PEPTIDES AND THEIR USES

(76) Inventors: Karl Kadler, 24 Waterside, Marple Stockport, Cheshire (GB) SK6 7LY; Neil Bulleid, 31 South Parade, Bramhall, Stockport (GB) SK7 3BJ; Gillian Ashcroft, 7 Broadhurst Lane, Wrightington, Lancs (GB) WN6 9RX ( * ) Notice: Subject to any disclaimer, the term of this patent is extended or adjusted under 35 U.S.C. 154(b) by 193 days.

(21) Appl. No.: 11/942,649

(22) Filed: Nov. 19, 2007

(65) Prior Publication Data
US 2008/0234176 A1 Sep. 25, 2008

Related U.S. Application Data

(62) Division of application No. 10/554,068, filed as application No. PCT/GB2004/001719 on Apr. 21, 2004, now Pat. No. 7,351,552.

(30) Foreign Application Priority Data
Apr. 22, 2003 (GB) .................. 0309064.4

(51) Int. Cl.
*C07K 14/00* (2006.01)
(52) U.S. Cl. .......................... 514/2; 530/350
(58) Field of Classification Search ........ None
See application file for complete search history.

(56) References Cited

U.S. PATENT DOCUMENTS 5,266,328 A 11/1993 Skubitz et al.
6,277,600 B1 8/2001 Tomita et al.

FOREIGN PATENT DOCUMENTS

| EP | 0 704 532 A2 | 4/1996 |
| EP | 0 747 068 A1 | 12/1996 |
| EP | 0 985 732 A2 | 3/2000 |
| EP | 1 234 581 A1 | 8/2002 |
| WO | WO 99/08311 A1 | 2/1999 |
| WO | WO 01/64031 A2 | 9/2001 |
| WO | WO 03/035692 A2 | 5/2003 |

*Primary Examiner*—Karen Cochrane Carlson
(74) *Attorney, Agent, or Firm*—Bose McKinney & Evans LLP

(57) ABSTRACT

A modified pro-α chain comprising a triple helix forming domain linked to at least an N-terminal domain, the N-terminal domain containing a polypeptide from at least part of a laminin glycoprotein or secretory leukocyte protease inhibitor. The pro-α chain may form part of a procollagen molecule that has the N-terminal domain retained. The procollagen molecule may be incorporated into collagen polymers, matrices and gels and be used for such applications as wound healing.

19 Claims, 15 Drawing Sheets

```
                                        atgatgagct tgtgcaaaa ggggagctgg
ctacttctcg ctctgcttca tcccactatt attttggcaa catctctgtc cttgtttctc
caaaggccca actcaagaga aaatggggGT actgagaata tgtttgtgat gtaccttgga
aataaagatg cctcccggga ctacatcggc atggcagttg tggatggcca gctcacctgt
gtctacaacc tggggaccg tgaggctgaa ctccaagtgg accagatctt gaccaagagt
gagactaagg aggcagttat ggatcgggtg aaatttcaga gaatttatca gtttgcaagg
cttaattaca ccaaaggagc cacatccagt aaaccagaaa cacccggagt ctatgacatg
gatggtagaa atagcaatac actccttaat ttggatcctg aaaatgttgt attttatgtt
ggaggttacc cacctgattt taaacttccc agtcgactaa gtttccctcc atacaaaggt
tgtattgaat tagatgacct caatgaaaat gttctgagct tgtacaactt caaaaaaaca
ttcaatctca acacaactga agtggagcct tgtagaagga ggaaggaaga gtcagacaaa
aattattttg aaggtacggg ctatgctcga gttccaactc aaccacatgc tcccatccca
acctttggac agacaattca gaccaccgtg gatagaggct tgctgttctt tgcagaaaac
ggggatcgct tcatatctct aaatatagaa gatggcaagc tcatggtgag atacaaactg
aattcagagc taccaaaaga gagaggagtt ggagacgcca taaacaacgg cagagaccat
tcgattcaga tcaaaattgg aaaactccaa aagcgtatgt ggataaatgt ggacgttcaa
aacactataa ttgatggtga agtatttgat ttcagcacat attatctggg aggaattcca
attgcaatca gggaagatt taacatttct acgcctgctt ccgaggctg catgaaaaat
ttgaagaaaa ccagtggtgt cgttagattg aatgatactg tgggagtaac caaaaagtgc
tcggaagact ggaagcttgt gcgatctgcc tcattctcca gaggaggaca attgagtttc
actgatttgg gcttaccacc tactgaccac ctccaggcct catttggatt tcagaccttt
caacccagtg gcatattatt agatcatcag acatggacaa ggaacctgca ggtcactctg
gaagatggtt acattgaatt gagcaccagc gatagcggcg gcccaatttt taaatctcca
cagacgtata tggatggttt actgcattat gtatctgtaa taagcgacaa ctctggacta
cggcttctca tcgatgacca gcttctgaga aatagcaaaa ggctaaaaca catttcaagt
tcccggcagt ctctgcgtct gggcgggagc aattttgagg gttgtattag caatgttttt
gtccagaggt tatcactgag tcctgaagtc ctagatttga ccagtaactc tctcaagaga
gatgtgtccc tgggaggctg cagtttaaac aaaccacctt ttctaatgtt gcttaaaggt
tctaccaggt ttaacaagac caagactttt cgtatcaacc agctgttgca ggacacacca
gtggcctccc caaggagcgt gaaggtgtgg caagatgcta atggtcaagg acctcaaggc
cccaagggag atccaggccc tcctggtatt cctgggagaa atggtgaccc tggtattcca
ggacaaccag ggtcccctgg ttctcctggc ccccctggaa tctgtgaatc atgccctact
ggtcctcaga actattctcc ccagtatgat tcatatgatg tcaagtctgg agtagcagta
ggaggactcg caggctatcc tggaccagct ggccccccag gccctcccgg tcccctggt
acatctggtc atcctggttc ccctggatct ccaggatacc aaggaccccc tggtgaacct
gggcaagctg gtccttcagg ccctccagga cctcctggtg ctataggtcc atctggtcct
gctggaaaag atggagaatc aggtagaccc ggacgacctg gagagcagg attgcctgga
cctccaggta tcaaaggtcc agctgggata cctggattcc ctggtatgaa aggacacaga
ggcttcgatg gacgaaatgg agaaaggggt gaaacaggtg ctcctggatt aaagggtgaa
aatggtcttc caggcgaaaa tggagctcct ggacccatgg gtccaagagg ggctcctggt
gagcgaggac ggccaggact tcctggggct gcaggtgctc ggggtaatga cggtgctcga
ggcagtgatg gtcaaccagg ccctcctggt cctcctggaa ctgccggatt ccctggatcc
cctggtgcta agggtgaagt tggacctgca gggtctcctg gttcaaatgg tgccctgga
caaagaggag aacctggacc tcagggacac gctggtgctc aaggtcctcc tggcccctct
gggattaatg gtagtcctgg tggtaaaggc gaaatgggtc ccgctggcat tctggagct
cctggactga tgggagcccg gggtcctcca ggaccagccg tgctaatgg tgctcctgga
ctgcgaggtg gtcaggtga gcctggtaag aatggtgcca aggagagcc cggaccacgt
ggtgaacgcg gtgaggctgg tattccaggt gttccaggag ctaaaggcga agatggcaag
gatggatcac ctggagaacc tggtgcaaat gggcttccag gagctgcagg agaaaggggt
gccctgggt tccgaggacc tgctggacca aatggcatcc aggagaaaa gggtcctgct
ggagagcgtg gtgctccagg ccctgcaggg ccagaggag ctgctggaga acctggcaga
gatggcgtcc ctggaggtcc aggaatgagg gcatgcccg gaagtccagg aggaccagga
agtgatggga aaccagggcc tcccggaagt caaggagaaa gtggtcgacc aggtcctcct
gggccatctg gtccccgagg tcagcctggt gtcatgggct cccaggtcc taaaggaaat
```

FIG. 3

```
gatggtgctc ctggtaagaa tggagaacga ggtggccctg gaggacctgg ccctcagggt
cctcctggaa agaatggtga aactggacct caaggacccc cagggcctac tgggcctggt
ggtgacaaag gagacacagg accccctggt ccacaaggat tacaaggctt gcctggtaca
ggtggtcctc caggagaaaa tggaaaacct ggggaaccag gtccaaaggg tgatgccggt
gcacctggag ctccaggagg caaggtgat gctggtgccc ctggtgaacg tggacctcct
ggattggcag gggccccagg acttagaggt ggagctggtc ccctggtcc cgaaggagga
aagggtgctg ctggtcctcc tgggccacct ggtgctgctg gtactcctgg tctgcaagga
atgcctggag aaagaggagg tcttggaagt cctggtccaa agggtgacaa gggtgaacca
ggcggcccag gtgctgatgg tgtcccaggg aaagatggcc caaggggtcc tactggtcct
attggtcctc ctggcccagc tggccagcct ggagataagg gtgaaggtgg tgccccgga
cttccaggta tagctggacc tcgtggtagc cctggtgaga gaggtgaaac tggccctcca
ggacctgctg gtttccctgg tgctcctgga cagaatggtg aacctggtgg taaaggagaa
agagggctc cgggtgagaa aggtgaagga ggccctcctg gagttgcagg acccctgga
ggttctggac ctgctggtcc tcctggtccc caaggtgtca aggtgaacg tggcagtcct
ggtggacctg gtgctgctgg cttccctggt gctcgtggtc ttcctggtcc tcctggtagt
aatggtaacc caggaccccc aggtcccagc ggttctccag gcaaggatgg gccccaggt
cctgcgggta acactggtgc tcctggcagc cctggagtgt ctggaccaaa aggtgatgct
ggccaaccag gagagaaggg atcgcctggt gcccagggcc caccaggagc tccaggccca
cttgggattg ctgggatcac tggagcacgg ggtcttgcag gaccaccagg catgccaggt
cctaggggaa gccctggccc tcagggtgtc aagggtgaaa gtggaaaacc aggagctaac
ggtctcagtg gagaacgtgg tccccctgga cccagggtc ttcctggtct ggctggtaca
gctggtgaac ctggaagaga tggaaaccct ggatcagatg gtcttccagg ccgagatgga
tctcctggtg gcaagggtga tcgtggtgaa aatggctctc ctggtgcccc tgcgctcct
ggtcatccag gcccacctgg tcctgtcggt ccagctggaa agagtggtga cagaggagaa
agtggccctg ctggccctgc tggtgctccc ggtcctgctg gttcccgagg tgctcctggt
cctcaaggcc cacgtggtga caaggtgaaa acaggtgaac gtggagctgc tggcatcaaa
ggacatcgag gattccctgg taatccaggt gccccaggtt ctccaggccc tgctggtcag
cagggtgcaa tcggcagtcc aggacctgca ggccccagag gacctgttgg acccagtgga
cctcctggca aagatggaac cagtggacat ccaggtccca ttggaccacc agggcctcga
ggtaacagag gtgaaagagg atctgagggc tccccaggcc acccaggca accaggccct
cctggacctc ctggtgcccc tggtccttgc tgtggtggtg ttggagccgc tgccattgct
gggattggag gtgaaaaagc tggcggtttt gccccgtatt atggagatga accaatggat
ttcaaaatca acaccgatga gattatgact tcactcaagt ctgttaatgg acaaatagaa
agcctcatta gtcctgatgg ttctcgtaaa aaccccgcta gaaactgcag agacctgaaa
ttctgccatc ctgaactcaa gagtggagaa tactgggttg accctaacca aggatgcaaa
ttggatgcta tcaaggtatt ctgtaatatg gaaactgggg aaacatgcat aagtgccaat
cctttgaatg ttccacggaa acactggtgg acagattcta gtgctgagaa gaaacacgtt
tggtttggag agtccatgga tggtggtttt cagtttagct acggcaatcc tgaacttcct
gaagatgtcc ttgatgtgca gctggcattc cttcgacttc tctccagccg agcttcccag
aacatcacat atcactgcaa aaatagcatt gcatacatgg atcaggccag tggaaatgta
aagaaggccc tgaagctgat ggggtcaaat gaaggtgaat tcaaggctga aggaaatagc
aaattcacct acacagttct ggaggatggt tgcacgaaac acactgggga atggagcaaa
acagtctttg aatatcgaac acgcaaggct gtgagactac ctattgtaga tattgcaccc
tatgacattg gtggtcctga tcaagaattt ggtgtggacg ttggccctgt ttgcttttta
taa
```

```
                                                                At gatgagcttt
gtgcaaaagg ggagctggct acttctcgct ctgcttcatc ccactattat tttggcatgc
tcggaagact ggaagcttgt gcgatctgcc tcattctcca gaggaggaca attgagtttc
actgatttgg gcttaccacc tactgaccac ctccaggcct catttggatt tcagacctttt
caacccagtg gcatattatt agatcatcag acatggacaa ggaacctgca ggtcactctg
gaagatggtt acattgaatt gagcaccagc gatagcggcg gcccaatttt taaatctcca
cagacgtata tggatggttt actgcattat gtatctgtaa taagcgacaa ctctggacta
cggcttctca tcgatgacca gcttctgaga aatagcaaaa ggctaaaaca catttcaagt
tcccggcagt ctctgcgtct gggcgggagc aattttgagg gttgtattag caatgttttt
gtccagaggt tatcactgag tcctgaagtc ctagatttga ccagtaactc tctcaagaga
gatgtgtccc tgggaggctg cagtttaaac aaaccaccttt ttctaatgtt gcttaaaggt
tctaccaggt ttaacaagac caagactttt cgtatcaacc agctgttgca ggacacacca
gtggcctccc caaggagcgt gaaggtgtgg caagatgcta atggtcaagg acctcaaggc
cccaagggag atccaggccc tcctggtatt cctgggagaa atggtgaccc tggtattcca
ggacaaccag ggtcccctgg ttctcctggc cccctggaa tctgtgaatc atgccctact
ggtcctcaga actattctcc ccagtatgat tcatatgatg tcaagtctgg agtagcagta
ggaggactcg caggctatcc tggaccagct ggcccccag gccctcccgg tccccctggt
acatctggtc atcctggttc ccctggatct ccaggatacc aaggacccc tggtgaacct
gggcaagctg gtccttcagg ccctccagga cctcctggtg ctataggtcc atctggtcct
gctggaaaag atggagaatc aggtagaccc ggacgacctg gagagcgagg attgcctgga
cctccaggta tcaaaggtcc agctgggata cctggattcc ctggtatgaa aggacacaga
ggcttcgatg gacgaaatgg agaaaagggt gaaacaggtg ctcctggatt aaagggtgaa
aatggtcttc caggcgaaaa tggagctcct ggacccatgg gtccaagagg ggctcctggt
gagcgaggac ggccaggact tcctggggct gcaggtgctc ggggtaatga cggtgctcga
ggcagtgatg gtcaaccagg ccctcctggt cctcctggaa ctgccggatt ccctggatcc
cctggtgcta agggtgaagt tggacctgca gggtctcctg gttcaaatgg tgcccctgga
caaagaggag aacctggacc tcagggacac gctggtgctc aaggtcctcc tggccctcct
gggattaatg gtagtcctgg tggtaaaggc gaaatgggtc ccgctggcat tcctggagct
cctggactga tgggagcccg ggtcctcca ggaccagccg gtgctaatgg tgctcctgga
ctgcgaggtg gtgcaggtga gcctggtaag aatggtgcca aggagagcc cggaccacgt
ggtgaacgcg gtgaggctgg tattccaggt gttccaggag ctaaaggcga agatggcaag
gatggatcac ctggagaacc tggtgcaaat gggcttccag gagctgcagg agaaagggt
gcccctgggt tccgaggacc tgctggacca aatggcatcc aggagaaaa gggtcctgct
ggagagcgtg gtgctccagg ccctgcaggg cccagaggag ctgctggaga acctggcaga
gatggcgtcc ctggaggtcc aggaatgagg ggcatgcccg gaagtccagg aggaccagga
agtgatggga accagggcc tcccggaagt caaggagaaa gtggtcgacc aggtcctcct
gggccatctg gtccccgagg tcagcctggt gtcatgggct tccccggtcc taaaggaaat
gatggtgctc ctggtaagaa tggagaacga ggtggccctg gaggacctgg ccctcagggt
cctcctggaa agaatggtga aactggacct caaggacccc agggcctac tgggcctggt
ggtgacaaag gagacacagg accccctggt ccacaaggat tacaaggctt gcctggtaca
ggtggtcctc caggagaaaa tggaaaacct ggggaaccag gtccaaaggg tgatgccggt
gcacctggag ctccaggagg caagggtgat gctggtgccc ctggtgaacg tggacctcct
ggattggcag ggcccccagg acttagaggt ggagctggtc cccctggtcc cgaaggagga
aagggtgctg ctggtcctcc tgggccacct ggtgctgctg gtactcctgg tctgcaagga
atgcctggag aaagaggagg tcttggaagt cctggtccaa gggtgacaa gggtgaacca
ggcggcccag gtgctgatgg tgtcccaggg aaagatggcc caaggggtcc tactggtcct
attggtcctc ctggcccagc tggccagcct ggagataagg gtgaaggtgg tgcccccgga
cttccaggta tagctggacc tcgtggtagc cctggtgaga gaggtgaaac tggccctcca
ggacctgctg gtttccctgg tgctcctgga cagaatggtg aacctggtgg taaaggagaa
agagggctc cgggtgagaa aggtgaagga ggccctcctg gagttgcagg acccccctgga
ggttctggac ctgctggtcc tcctggtccc caaggtgtca aggtgaacg tggcagtcct
ggtggacctg gtgctgctgg cttccctggt gctcgtggtc ttcctggtcc tcctggtagt
aatggtaacc caggacccc aggtcccagc ggttctccag gcaaggatgg gccccaggt
cctgcgggta acactggtgc tcctggcagc cctggagtgt ctggaccaaa aggtgatgct
```

FIG. 6

```
ggccaaccag gagagaaggg atcgcctggt gcccagggcc caccaggagc tccaggccca
cttgggattg ctgggatcac tggagcacgg ggtcttgcag gaccaccagg catgccaggt
cctaggggaa gccctggccc tcagggtgtc aagggtgaaa gtgggaaacc aggagctaac
ggtctcagtg gagaacgtgg tccccctgga ccccagggtc ttcctggtct ggctggtaca
gctggtgaac ctggaagaga tggaaaccct ggatcagatg gtcttccagg ccgagatgga
tctcctggtg gcaagggtga tcgtggtgaa aatggctctc ctggtgcccc tggcgctcct
ggtcatccag gcccacctgg tcctgtcggt ccagctggaa agagtggtga cagaggagaa
agtggccctg ctggccctgc tggtgctccc ggtcctgctg gttcccgagg tgctcctggt
cctcaaggcc cacgtggtga caaaggtgaa acaggtgaac gtggagctgc tggcatcaaa
ggacatcgag gattccctgg taatccaggt gccccaggtt ctccaggccc tgctggtcag
cagggtgcaa tcggcagtcc aggacctgca ggccccagag gacctgttgg acccagtgga
cctcctggca aagatggaac cagtggacat ccaggtccca ttggaccacc agggcctcga
ggtaacagag gtgaagagg atctgagggc tccccaggcc acccagggca accaggccct
cctggacctc ctggtgcccc tggtccttgc tgtggtggtg ttggagccgc tgccattgct
gggattggag gtgaaaaagc tggcggtttt gccccgtatt atggagatga accaatggat
ttcaaaatca acaccgatga gattatgact tcactcaagt ctgttaatgg acaaatagaa
agcctcatta gtcctgatgg ttctcgtaaa aaccccgcta gaaactgcag agacctgaaa
ttctgccatc ctgaactcaa gagtggagaa tactgggttg accctaacca aggatgcaaa
ttggatgcta tcaaggtatt ctgtaatatg gaaactgggg aaacatgcat aagtgccaat
cctttgaatg ttccacggaa acactggtgg acagattcta gtgctgagaa gaaacacgtt
tggtttggag agtccatgga tggtggtttt cagtttagct acggcaatcc tgaacttcct
gaagatgtcc ttgatgtgca gctggcattc cttcgacttc tctccagccg agcttccag
aacatcacat atcactgcaa aaatagcatt gcatacatgg atcaggccag tggaaatgta
aagaaggccc tgaagctgat ggggtcaaat gaaggtgaat tcaaggctga aggaaatagc
aaattcacct acacagttct ggaggatggt tgcacgaaac acactgggga atggagcaaa
acagtctttg aatatcgaac acgcaaggct gtgagactac ctattgtaga tattgcaccc
tatgacattg gtggtcctga tcaagaattt ggtgtggacg ttggccctgt ttgcttttta
taa
```

```
atgaagtc    cagcggcctc   ttcccttcc   tggtgctgct   tgccctggga
actctggcac  cttgggctgt   ggaaggctct  ggaaagtcct   tcaaagctgg
agtctgtcct  cctaagaaat   ctgccagtg   ccttagatac   aagaaacctg
agtgccagag  tgactggcag   tgtccaggga  agaagagatg   ttgtcctgac
acttgtggca  tcaaatgcct   ggatcctgtt  gacacccaa    acccaacaag
gaggaagcct  gggaagtgcc   cagtgactta  tggccaatgt   ttgatgctta
acccccccaa  tttctgtgag   atggatggcc  agtgcaagcg   tgacttgaag
tgttgcatgg  gcatgtgtgg   gaaatcctgc  gtttccctg    tgaaagct gctgt       tgaaggagga   tgttcccatc  ttggtcagtc   ctatgcggat
agagatgtct  ggaagccaga   accatgccaa  atatgtgtct   gtgactcagg
atccgttctc  tgcgatgaca   taatatgtga  cgatcaagaa   ttagactgcc
ccaacccaga  aattccattt   ggagaatgtt  gtgcagtttg   cccacagcct
ccaactgctc  ctactcgccc   tcctaatggt  caaggacctc   aaggccccaa
gggagatcca  ggccctcctg   gtattcctgg  gagaaatggt   gaccctggta
ttccaggaca  accagggtcc   cctggttctc  ctggcccccc   tggaatctgt
gaatcatgcc  ctactggtcc   tcagaactat  tctccccagt   atgattcata
tgatgtcaag  tctggagtag   cagtaggagg  actcgcaggc   tatcctggac
cagctggccc  cccaggccct   cccggtcccc  ctggtacatc   tggtcatcct
ggttcccctg  gatctccagg   ataccaagga  cccctggtg    aacctgggca
agctggtcct  tcaggccctc   caggacctcc  tggtgctata   ggtccatctg
gtcctgctgg  aaaagatgga   gaatcaggta  gacccggacg   acctggagag
cgaggattgc  ctggacctcc   aggtatcaaa  ggtccagctg   ggatacctgg
attccctggt  atgaaaggac   acagaggctt  cgatggacga   aatggagaaa
agggtgaaac  aggtgctcct   ggattaaagg  gtgaaaatgg   tcttccaggc
gaaaatggag  ctcctggacc   catgggtcca  agagggctc    ctggtgagcg
aggacggcca  ggacttcctg   gggctgcagg  tgctcggggt   aatgacggtg
ctcgaggcag  tgatggtcaa   ccaggccctc  ctggtcctcc   tggaactgcc
ggattccctg  gatccctgg    tgctaagggt  gaagttggac   ctgcagggtc
tcctggttca  aatggtgccc   ctggacaaag  aggagaacct   ggacctcagg
gacacgctgg  tgctcaaggt   cctcctggcc  ctcctgggat   taatggtagt
cctggtggta  aaggcgaaat   gggtcccgct  ggcattcctg   gagctcctgg
actgatggga  gcccggggtc   ctccaggacc  agccggtgct   aatggtgctc
ctggactgcg  aggtggtgca   ggtgagcctg  gtaagaatgg   tgccaaagga
gagcccggac  cacgtggtga   acgcggtgag  gctggtattc   caggtgttcc
aggagctaaa  ggcgaagatg   gcaaggatgg  atcacctgga   gaacctggtg
caaatgggct  tccaggagct   gcaggagaaa  ggggtgcccc   tgggttccga
ggacctgctg  gaccaaatgg   catcccagga  gaaagggtc    ctgctggaga
gcgtggtgct  ccaggccctg   cagggcccag  aggagctgct   ggagaacctg
gcagagatgg  cgtcctgga    ggtccaggaa  tgaggggcat   gccggaagt
ccaggaggac  caggaagtga   tgggaaacca  gggcctcccg   gaagtcaagg
agaaagtggt  cgaccaggtc   ctcctgggcc  atctggtccc   cgaggtcagc
ctggtgtcat  gggcttcccc   ggtcctaaag  gaaatgatgg   tgctcctggt
```

FIG.8

```
aagaatggag aacgaggtgg ccctggagga cctggccctc agggtcctcc
tggaaagaat ggtgaaactg gacctcaagg accccaggg cctactgggc
ctggtggtga caaaggagac acaggacccc ctggtccaca aggattacaa
ggcttgcctg gtacaggtgg tcctccagga gaaatggaa aacctgggga
accaggtcca aagggtgatg ccggtgcacc tggagctcca ggaggcaagg
gtgatgctgg tgccctggt gaacgtggac ctcctggatt ggcaggggcc
ccaggactta gaggtggagc tggtcccct ggtcccgaag gaggaaaggg
tgctgctggt cctcctgggc cacctggtgc tgctggtact cctggtctgc
aaggaatgcc tggagaaaga ggaggtcttg gaagtcctgg tccaagggt
gacaagggtg aaccaggcgg cccaggtgct gatggtgtcc cagggaaaga
tggcccaagg ggtcctactg gtcctattgg tcctcctggc ccagctggcc
agcctggaga taagggtgaa ggtggtgccc ccggacttcc aggtatagct
ggacctcgtg gtagccctgg tgagagaggt gaaactggcc ctccaggacc
tgctggtttc cctggtgctc ctggacagaa tggtgaacct ggtggtaaag
gagaaagagg ggctccgggt gagaaggtg aaggaggccc tcctggagtt
gcaggacccc ctggaggttc tggacctgct ggtcctcctg gtccccaagg
tgtcaaaggt gaacgtggca gtcctggtgg acctggtgct gctggcttcc
ctggtgctcg tggtcttcct ggtcctcctg gtagtaatgg taacccagga
cccccaggtc ccagcggttc tccaggcaag gatgggcccc caggtcctgc
gggtaacact ggtgctcctg gcagcctgg agtgtctgga ccaaaaggtg
atgctggcca accaggagag aagggatcgc ctggtgccca gggcccacca
ggagctccag gcccacttgg gattgctggg atcactggag cacggggtct
tgcaggacca ccaggcatgc caggtcctag gggaagccct ggccctcagg
gtgtcaaggg tgaaagtggg aaaccaggag ctaacggtct cagtggagaa
cgtggtcccc ctggaccca gggtcttcct ggtctggctg gtacagctgg
tgaacctgga agagatggaa accctggatc agatggtctt ccaggccgag
atggatctcc tggtggcaag ggtgatcgtg gtgaaaatgg ctctcctggt
gcccctggcg ctcctggtca tccaggccca cctggtcctg tcggtccagc
tggaaagagt ggtgacagag gagaaagtgg ccctgctggc cctgctggtg
ctcccggtcc tgctggttcc cgaggtgctc ctggtcctca aggcccacgt
ggtgacaaag gtgaaacagg tgaacgtgga gctgctggca tcaaaggaca
tcgaggattc cctggtaatc caggtgcccc aggttctcca ggccctgctg
gtcagcaggg tgcaatcggc agtccaggac ctgcaggccc cagaggacct
gttggaccca gtggacctcc tggcaaagat ggaaccagtg gacatccagg
tcccattgga ccaccagggc ctcgaggtaa cagaggtgaa agaggatctg
agggctcccc aggccaccca gggcaaccag gccctcctgg acctcctggt
gccctggtc cttgctgtgg tggtgttgga gccgctgcca ttgctgggat
tggaggtgaa aaagctggcg gttttgcccc gtattatgga gatgaaccaa
tggatttcaa aatcaacacc gatgagatta tgacttcact caagtctgtt
aatggacaaa tagaaagcct cattagtcct gatggttctc gtaaaaaccc
cgctagaaac tgcagagacc tgaaattctg ccatcctgaa ctcaagagtg
gagaatactg ggttgaccct aaccaaggat gcaaattgga tgctatcaag
gtattctgta atatggaaac tggggaaaca tgcataagtg ccaatccttt
gaatgttcca cggaaacact ggtggacaga ttctagtgct gagaagaaac
acgtttggtt tggagagtcc atggatggtg gttttcagtt tagctacggc
aatcctgaac ttcctgaaga tgtccttgat gtgcagctgg cattccttcg
acttctctcc agccgagctt cccagaacat cacatatcac tgcaaaaata
gcattgcata catggatcag gccagtggaa atgtaaagaa ggcctgaag
ctgatggggt caaatgaagg tgaattcaag gctgaaggaa atagcaaatt
```

FIG. 8 cont;

```
cacctacaca gttctggagg atggttgcac gaaacacact ggggaatgga
gcaaaacagt ctttgaatat cgaacacgca aggctgtgag actacctatt
gtagatattg caccctatga cattggtggt cctgatcaag aatttggtgt
ggacgttggc cctgtttgct ttttataa
```

FIG. 8 cont;

```
Met K S S G L F P P F L V L L A L G T L A P W A V E G S G K S
F K A G V C P P K K S A Q C L R Y K K P E C Q S D W Q C P G
K K R C C P D T C G I K C L D P V D T P N P T R R K P G K C
P V T Y G Q C L Met L N P P N F C E Met D G Q C K R D L K C
C Met G Met C G K S C V S P V K A

A V E G G C S H L G Q S Y A D R D V W K P E P C Q I C V C D
S G S V L C D D I I C D D Q E L D C P N P E I P F G E C C A
V C P Q P P T A P T R P P N G Q G P Q G P K G D P G P P G I
P G R N G D P G I P G Q P G S P G S P G P P G I C E S C P T
G P Q N Y S P Q Y D S Y D V K S G V A V G G L A G Y P G P A
G P P G P P G P P G T S G H P G S P G S P G Y Q G P P G E P
G Q A G P S G P P G P P G A I G P S G P A G K D G E S G R P
G R P G E R G L P G P P G I K G P A G I P G F P G Met K G H
R G F D G R N G E K G E T G A P G L K G E N G L P G E N G A
P G P Met G P R G A P G E R G R P G L P G A A G A R G N D G
A R G S D G Q P G P P G P P G T A G F P G S P G A K G E V G
P A G S P G S N G A P G Q R G E P G P Q G H A G A Q G P P G
P P G I N G S P G G K G E Met G P A G I P G A P G L Met G A
R G P P G P A G A N G A P G L R G G A G E P G K N G A K G E
P G P R G E R G E A G I P G V P G A K G E D G K D G S P G E
P G A N G L P G A A G E R G A P G F R G P A G P N G I P G E
K G P A G E R G A P G P A G P R G A A G E P G R D G V P G G
P G Met R G Met P G S P G G P G S D G K P G P P G S Q G E S
G R P G P P G P S G P R G Q P G V Met G F P G P K G N D G A
P G K N G E R G G P G G P G P Q G P P G K N G E T G P Q G P
P G P T G P G G D K G D T G P P G P Q G L Q G L P G T G G P
P G E N G K P G E P G P K G D A G A P G A P G G K G D A G A
P G E R G P P G L A G A P G L R G G A G P P G P E G G K G A
A G P P G P P G A A G T P G L Q G Met P G E R G G L G S P G
P K G D K G E P G G P G A D G V P G K D G P R G P T G P I G
P P G P A G Q P G D K G E G G A P G L P G I A G P R G S P G
E R G E T G P P G P A G F P G A P G Q N G E P G G K G E R G
A P G E K G E G G P P G V A G P P G G S G P A G P P G P Q G
V K G E R G S P G G P G A A G F P G A R G L P G P P G S N G
N P G P P G P S G S P G K D G P P G P A G N T G A P G S P G
V S G P K G D A G Q P G E K G S P G A Q G P P G A P G P L G
I A G I T G A R G L A G P P G Met P G P R G S P G P Q G V K
G E S G K P G A N G L S G E R G P P G P Q G L P G L A G T A
G E P G R D G N P G S D G L P G R D G S P G G K G D R G E N
G S P G A P G A P G H P G P P G P V G P A G K S G D R G E S
```

FIG. 9

```
G P A G P A G A P G P A G S R G A P G P Q G P R G D K G E T
G E R G A A G I K G H R G F P G N P G A P G S P G P A G Q Q
G A I G S P G P A G P R G P V G P S G P P G K D G T S G H P
G P I G P P G P R G N R G E R G S E G S P G H P G Q P G P P
G P P G A P G P C C G G V G A A A I A G I G G E K A G G F A
P Y Y G D E P Met D F K I N T D E I Met T S L K S V N G Q I
E S L I S P D G S R K N P A R N C R D L K F C H P E L K S G
E Y W V D P N Q G C K L D A I K V F C N Met E T G E T C I S
A N P L N V P R K H W W T D S S A E K K H V W F G E S Met D
G G F Q F S Y G N P E L P E D V L D V Q L A F L R L L S S R
A S Q N I T Y H C K N S I A Y Met D Q A S G N V K K A L K L
Met G S N E G E F K A E G N S K F T Y T V L E D G C T K H T
G E W S K T V F E Y R T R K A V R L P I V D I A P Y D I G G
P D Q E F G V D V G P V C F L Stop
```

FIG. 9 cont;

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide for PCR

<400> SEQUENCE: 1
aattaaccct cactaaaggg                                            20

<210> SEQ ID NO 2
<211> LENGTH: 31
<212> TYPE: DNA
<213> ORGANISM: Artificial Sequence
<220> FEATURE:
<223> OTHER INFORMATION: Oligonucleotide for PCR

<400> SEQUENCE: 2
acagagatgt tgccaaaata atagtgggat g                               31

<210> SEQ ID NO 3
<211> LENGTH: 31
<212> TYPE: DNA
<213> ORGANISM: Artificial Sequence
<220> FEATURE:
<223> OTHER INFORMATION: Oligonucleotide for PCR

<400> SEQUENCE: 3
tattttggca acatctctgt ccttgtttct c                               31

<210> SEQ ID NO 4
<211> LENGTH: 31
<212> TYPE: DNA
<213> ORGANISM: Artificial Sequence
<220> FEATURE:
<223> OTHER INFORMATION: Oligonucleotide for PCR

<400> SEQUENCE: 4
cttgaccatt agcatcttgc cacaccttca c                               31

<210> SEQ ID NO 5
<211> LENGTH: 31
<212> TYPE: DNA
<213> ORGANISM: Artificial Sequence
<220> FEATURE:
<223> OTHER INFORMATION: Oligonucleotide for PCR

<400> SEQUENCE: 5
gcaagatgct aatggtcaag gacctcaagg c                               31
```

```
<210> SEQ ID NO 6
<211> LENGTH: 20
<212> TYPE: DNA
<213> ORGANISM: Artificial Sequence
<220> FEATURE:
<223> OTHER INFORMATION: Oligonucleotide for PCR

<400> SEQUENCE: 6
agaccctgca ggtccaactt                                              20

<210> SEQ ID NO 7
<211> LENGTH: 32
<212> TYPE: DNA
<213> ORGANISM: Artificial Sequence
<220> FEATURE:
<223> OTHER INFORMATION: Oligonucleotide for PCR

<400> SEQUENCE: 7
gttgtaaaac ggcggccgct gaattgtaat ac                                32

<210> SEQ ID NO 8
<211> LENGTH: 32
<212> TYPE: DNA
<213> ORGANISM: Artificial Sequence
<220> FEATURE:
<223> OTHER INFORMATION: Oligonucleotide for PCR

<400> SEQUENCE: 8
gtattacaat tcagcggccg ccgttttaca ac                                32

<210> SEQ ID NO 9
<211> LENGTH: 5853
<212> TYPE: DNA
<213> ORGANISM: Artificial Sequence
<220> FEATURE:
<223> OTHER INFORMATION: DNA molecule based on procollagen type III
      N-propeptide. Sequence prior to N100 replaced with the sequence
      for the G123 domains of the alpha3 chain of laminin-5 whilst
      retaining the collagen III signal sequence.

<400> SEQUENCE: 9
atgatgagct ttgtgcaaaa ggggagctgg ctacttctcg ctctgcttca tcccactatt    60
attttggcaa catctctgtc cttgtttctc caaaggccca actcaagaga aatgggggt    120 actgagaata tgtttgtgat gtaccttgga aataaagatg cctcccggga ctacatcggc    180
atggcagttg tggatggcca gctcacctgt gtctacaacc tggggaccg tgaggctgaa    240 ctccaagtgg accagatctt gaccaagagt gagactaagg aggcagttat ggatcgggtg    300
aaatttcaga gaatttatca gtttgcaagg cttaattaca ccaaggagc cacatccagt    360 aaaccagaaa caccccggagt ctatgacatg gatggtagaa atagcaatac actccttaat    420
ttggatcctg aaaatgttgt attttatgtt ggaggttacc cacctgattt taaacttccc    480
agtcgactaa gtttccctcc atacaaaggt tgtattgaat tagatgacct caatgaaaat    540
gttctgagct tgtacaactt caaaaaaaca ttcaatctca acacaactga agtggagcct    600
tgtagaagga ggaaggaaga gtcagacaaa aattattttg aaggtacggg ctatgctcga    660
gttccaactc aaccacatgc tcccatccca acctttggac agacaattca gaccaccgtg    720
gatagaggct gctgttcttt gcagaaaac ggggatcgct tcatatctct aaatatagaa    780
gatggcaagc tcatggtgag atacaaactg aattcagagc taccaaaga gagaggagtt    840 ggagacgcca taacaacgg cagagaccat tcgattcaga tcaaaattgg aaaactccaa    900
aagcgtatgt ggataaatgt ggacgttcaa aacactataa ttgatggtga agtatttgat    960
```

-continued

```
ttcagcacat attatctggg aggaattcca attgcaatca gggaaagatt taacatttct  1020
acgcctgctt tccgaggctg catgaaaaat ttgaagaaaa ccagtggtgt cgttagattg  1080
aatgatactg tgggagtaac caaaaagtgc tcggaagact ggaagcttgt gcgatctgcc  1140
tcattctcca gaggaggaca attgagtttc actgatttgg gcttaccacc tactgaccac  1200
ctccaggcct catttggatt tcagacccttt caacccagtg gcatattatt agatcatcag  1260
acatggacaa ggaacctgca ggtcactctg gaagatggtt acattgaatt gagcaccagc  1320
gatagcggcg gcccaatttt taaatctcca cagacgtata tggatggttt actgcattat  1380
gtatctgtaa taagcgacaa ctctggacta cggcttctca tcgatgacca gcttctgaga  1440
aatagcaaaa ggctaaaaca catttcaagt tcccggcagt ctctgcgtct gggcgggagc  1500
aattttgagg gttgtattag caatgttttt gtccagaggt tatcactgag tcctgaagtc  1560
ctagatttga ccagtaactc tctcaagaga gatgtgtccc tgggaggctg cagtttaaac  1620
aaaccacctt ttctaatgtt gcttaaaggt tctaccaggt ttaacaagac caagactttt  1680
cgtatcaacc agctgttgca ggacacacca gtggcctccc caaggagcgt gaaggtgtgg  1740
caagatgcta atggtcaagg acctcaaggc cccaagggag atccaggccc tcctggtatt  1800
cctgggagaa atggtgaccc tggtattcca ggacaaccag ggtcccctgg ttctcctggc  1860
cccccctggaa tctgtgaatc atgccctact ggtcctcaga actattctcc ccagtatgat  1920
tcatatgatg tcaagtctgg agtagcagta ggaggactcg caggctatcc tggaccagct  1980
ggcccccag ccctcccgg tccccctggt acatctggtc atcctggttc ccctggatct  2040
ccaggatacc aaggacccccc tggtgaacct gggcaagctg gtccttcagg ccctccagga  2100
cctcctggtg ctataggtcc atctggtcct gctggaaaag atggagaatc aggtagaccc  2160
ggacgacctg gagagcgagg attgcctgga cctccaggta tcaaaggtcc agctgggata  2220
cctggattcc ctggtatgaa aggacacaga ggcttcgatg gacgaaatgg agaaagggt  2280
gaaacaggtg ctcctggatt aaagggtgaa atggtcttc caggcgaaaa tggagctcct  2340
ggacccatgg gtccaagagg ggctcctggt gagcgaggac ggccaggact tcctgggct  2400
gcaggtgctc ggggtaatga cggtgctcga ggcagtgatg gtcaaccagg ccctcctggt  2460
cctcctggaa ctgccggatt ccctggatcc cctggtgcta agggtgaagt tggacctgca  2520
gggtctcctg gttcaaatgg tgcccctgga caaagaggag aacctggacc tcagggacac  2580
gctggtgctc aaggtcctcc tggccctcct gggattaatg gtagtcctgg tggtaaaggc  2640
gaaatgggtc ccgctggcat tcctggagct cctggactga tgggagcccg ggtcctcca  2700
ggaccagccg gtgctaatgg tgctcctgga ctgcgaggtg gtgcaggtga gcctggtaag  2760
aatggtgcca aggagagcc cggaccacgt ggtgaacgcg gtgaggctgg tattccaggt  2820
gttccaggag ctaaaggcga agatggcaag gatggatcac tggagaacc tggtgcaaat  2880
gggcttccag gagctgcagg agaaaggggt gcccctgggt tccgaggacc tgctggacca  2940
aatggcatcc caggagaaaa gggtcctgct ggagagcgtg gtgctccagg ccctgcaggg  3000
cccagaggag ctgctggaga acctggcaga gatggcgtcc ctggaggtcc aggaatgagg  3060
ggcatgcccg gaagtccagg aggaccagga agtgatggga aaccaggcc tcccggaagt  3120
caaggagaaa gtggtcgacc aggtcctcct gggccatctg gtcccccgagg tcagcctggt  3180
gtcatgggct tccccggtcc taaaggaaat gatggtgctc ctggtaagaa tggagaacga  3240
ggtggccctg gaggacctgg ccctcagggt cctcctggaa agaatggtga aactggacct  3300
```

```
caaggacccc cagggcctac tgggcctggt ggtgacaaag gagacacagg acccctggt    3360
ccacaaggat tacaaggctt gcctggtaca ggtggtcctc caggagaaaa tggaaaacct   3420
ggggaaccag gtccaaaggg tgatgccggt gcacctggag ctccaggagg caagggtgat   3480
gctggtgccc ctggtgaacg tggacctcct ggattggcag gggcccccagg acttagaggt  3540
ggagctggtc cccctggtcc cgaaggagga aagggtgctg ctggtcctcc tgggccacct   3600
ggtgctgctg gtactcctgg tctgcaagga atgcctggag aaagaggagg tcttggaagt   3660
cctggtccaa agggtgacaa gggtgaacca ggcggcccag gtgctgatgg tgtcccaggg   3720
aaagatggcc caagggtgtcc tactggtcct attggtcctc ctggcccagc tggccagcct  3780
ggagataagg gtgaaggtgg tgccccggga cttccaggta tagctggacc tcgtggtagc   3840
cctggtgaga gaggtgaaac tggccctcca ggacctgctg gtttccctgg tgctcctgga   3900
cagaatggtg aacctggtgg taaggagaaa gaggggctc cgggtgagaa aggtgaagga    3960
ggccctcctg gagttgcagg acccctggga ggttctggac ctgctggtcc tcctggtccc   4020
caaggtgtca aggtgaacg tggcagtcct ggtggacctg gtgctgctgg cttccctggt    4080
gctcgtggtc ttcctggtcc tcctggtagt aatggtaacc caggacccccc aggtcccagc   4140
ggttctccag gcaaggatgg gccccaggt cctgcgggta acactggtgc tcctggcagc    4200
cctggagtgt ctggaccaaa aggtgatgct ggccaaccag gagagaaggg atcgcctggt   4260
gcccagggcc caccaggagc tccaggccca cttgggattg ctgggatcac tggagcacgg   4320
ggtcttgcag gaccaccagg catgccaggt cctaggggaa gccctggccc tcagggtgtc   4380
aagggtgaaa gtgggaaacc aggagctaac ggtctcagtg gagaacgtgg tccccctgga   4440
ccccagggtc ttcctggtct ggctggtaca gctggtgaac tggaagaga tggaaaccct    4500
ggatcagatg gtcttccagg ccgagatgga tctcctggtg gcaagggtga tcgtggtgaa   4560
aatggctctc ctggtgcccc tggcgctcct ggtcatccag gccacctgg tcctgtcggt    4620
ccagctggaa agagtggtga cagaggagaa agtggccctg ctggccctgc tggtgctccc   4680
ggtcctgctg gttcccgagg tgctcctggt cctcaaggcc cacgtggtga caaaggtgaa   4740
acaggtgaac gtggagctgc tggcatcaaa ggacatcgag gattccctgg taatccaggt   4800
gccccaggtt ctccaggccc tgctggtcag cagggtgcaa tcggcagtcc aggacctgca   4860
ggccccagag gacctgttgg acccagtgga cctcctggca agatggaac cagtggacat    4920
ccaggtccca ttggaccacc agggcctcga ggtaacagag gtgaagagg atctgagggc   4980
tccccaggcc acccagggca accaggccct cctggacctc ctggtgcccc tggtcccttgc  5040
tgtggtggtg ttggagccgc tgccattgct gggattggag gtgaaaaagc tggcggtttt   5100
gcccgtatt atggagatga accaatggat ttcaaaatca acaccgatga gattatgact    5160
tcactcaagt ctgttaatgg acaaatagaa agcctcatta gtcctgatgg ttctcgtaaa   5220
aacccccgcta gaaactgcag agacctgaaa ttctgccatc ctgaactcaa gagtggagaa   5280
tactgggttg accctaacca aggatgcaaa ttggatgcta tcaaggtatt ctgtaatatg   5340
gaaactgggg aaacatgcat aagtgccaat cctttgaatg ttccacggaa acactggtgg   5400
acagattcta gtgctgagaa gaaacacgtt tggtttggag agtccatgga tggtggtttt   5460
cagtttagct acggcaatcc tgaacttcct gaagatgtcc ttgatgtgca gctggcattc    5520
cttcgacttc tctccagccg agcttcccag aacatcacat atcactgcaa aaatagcatt    5580
gcatacatgg atcaggccag tggaaatgta aagaaggccc tgaagctgat ggggtcaaat    5640
gaaggtgaat tcaaggctga aggaaatagc aaattcacct acacagttct ggaggatggt   5700
```

-continued

```
tgcacgaaac acactgggga atggagcaaa acagtctttg aatatcgaac acgcaaggct    5760
gtgagactac ctattgtaga tattgcaccc tatgacattg gtggtcctga tcaagaattt    5820
ggtgtggacg ttggccctgt ttgcttttta taa                                 5853
```

<210> SEQ ID NO 10
<211> LENGTH: 1950
<212> TYPE: PRT
<213> ORGANISM: Artificial Sequence
<220> FEATURE:
<223> OTHER INFORMATION: Sequence of the modified pro-alpha chain

<400> SEQUENCE: 10

```
Met Met Ser Phe Val Gln Lys Gly Ser Trp Leu Leu Leu Ala Leu Leu
1               5                   10                  15

His Pro Thr Ile Ile Leu Ala Thr Ser Leu Ser Leu Phe Leu Gln Arg
            20                  25                  30

Pro Asn Ser Arg Glu Asn Gly Gly Thr Glu Asn Met Phe Val Met Tyr
        35                  40                  45

Leu Gly Asn Lys Asp Ala Ser Arg Asp Tyr Ile Gly Met Ala Val Val
    50                  55                  60

Asp Gly Gln Leu Thr Cys Val Tyr Asn Leu Gly Asp Arg Glu Ala Glu
65                  70                  75                  80

Leu Gln Val Asp Gln Ile Leu Thr Lys Ser Glu Thr Lys Glu Ala Val
                85                  90                  95

Met Asp Arg Val Lys Phe Gln Arg Ile Tyr Gln Phe Ala Arg Leu Asn
            100                 105                 110

Tyr Thr Lys Gly Ala Thr Ser Ser Lys Pro Glu Thr Pro Gly Val Tyr
        115                 120                 125

Asp Met Asp Gly Arg Asn Ser Asn Thr Leu Leu Asn Leu Asp Pro Glu
    130                 135                 140

Asn Val Val Phe Tyr Val Gly Gly Tyr Pro Pro Asp Phe Lys Leu Pro
145                 150                 155                 160

Ser Arg Leu Ser Phe Pro Pro Tyr Lys Gly Cys Ile Glu Leu Asp Asp
                165                 170                 175

Leu Asn Glu Asn Val Leu Ser Leu Tyr Asn Phe Lys Lys Thr Phe Asn
            180                 185                 190

Leu Asn Thr Thr Glu Val Glu Pro Cys Arg Arg Lys Glu Glu Ser
        195                 200                 205

Asp Lys Asn Tyr Phe Glu Gly Thr Gly Tyr Ala Arg Val Pro Thr Gln
    210                 215                 220

Pro His Ala Pro Ile Pro Thr Phe Gly Gln Thr Ile Gln Thr Thr Val
225                 230                 235                 240

Asp Arg Gly Leu Leu Phe Phe Ala Glu Asn Gly Asp Arg Phe Ile Ser
                245                 250                 255

Leu Asn Ile Glu Asp Gly Lys Leu Met Val Arg Tyr Lys Leu Asn Ser
            260                 265                 270

Glu Leu Pro Lys Glu Arg Gly Val Gly Asp Ala Ile Asn Asn Gly Arg
        275                 280                 285

Asp His Ser Ile Gln Ile Lys Ile Gly Lys Leu Gln Lys Arg Met Trp
    290                 295                 300

Ile Asn Val Asp Val Gln Asn Thr Ile Ile Asp Gly Glu Val Phe Asp
305                 310                 315                 320

Phe Ser Thr Tyr Tyr Leu Gly Gly Ile Pro Ile Ala Ile Arg Glu Arg
                325                 330                 335
```

-continued

```
Phe Asn Ile Ser Thr Pro Ala Phe Arg Gly Cys Met Lys Asn Leu Lys
            340                 345                 350

Lys Thr Ser Gly Val Val Arg Leu Asn Asp Thr Val Gly Val Thr Lys
        355                 360                 365

Lys Cys Ser Glu Asp Trp Lys Leu Val Arg Ser Ala Ser Phe Ser Arg
    370                 375                 380

Gly Gly Gln Leu Ser Phe Thr Asp Leu Gly Leu Pro Pro Thr Asp His
385                 390                 395                 400

Leu Gln Ala Ser Phe Gly Phe Gln Thr Phe Gln Pro Ser Gly Ile Leu
                405                 410                 415

Leu Asp His Gln Thr Trp Thr Arg Asn Leu Gln Val Thr Leu Glu Asp
            420                 425                 430

Gly Tyr Ile Glu Leu Ser Thr Asp Ser Gly Pro Ile Phe Lys
        435                 440                 445

Ser Pro Gln Thr Tyr Met Asp Gly Leu Leu His Tyr Val Ser Val Ile
    450                 455                 460

Ser Asp Asn Ser Gly Leu Arg Leu Leu Ile Asp Asp Gln Leu Leu Arg
465                 470                 475                 480

Asn Ser Lys Arg Leu Lys His Ile Ser Ser Arg Gln Ser Leu Arg
                485                 490                 495

Leu Gly Gly Ser Asn Phe Glu Gly Cys Ile Ser Asn Val Phe Val Gln
            500                 505                 510

Arg Leu Ser Leu Ser Pro Glu Val Leu Asp Leu Thr Ser Asn Ser Leu
        515                 520                 525

Lys Arg Asp Val Ser Leu Gly Gly Cys Ser Leu Asn Lys Pro Pro Phe
    530                 535                 540

Leu Met Leu Leu Lys Gly Ser Thr Arg Phe Asn Lys Thr Lys Thr Phe
545                 550                 555                 560

Arg Ile Asn Gln Leu Leu Gln Asp Thr Pro Val Ala Ser Pro Arg Ser
                565                 570                 575

Val Lys Val Trp Gln Asp Ala Asn Gly Gln Gly Pro Gln Gly Pro Lys
            580                 585                 590

Gly Asp Pro Gly Pro Gly Ile Pro Gly Arg Asn Gly Asp Pro Gly
        595                 600                 605

Ile Pro Gly Gln Pro Gly Ser Pro Gly Ser Pro Gly Pro Gly Ile
    610                 615                 620

Cys Glu Ser Cys Pro Thr Gly Pro Gln Asn Tyr Ser Pro Gln Tyr Asp
625                 630                 635                 640

Ser Tyr Asp Val Lys Ser Gly Val Ala Val Gly Gly Leu Ala Gly Tyr
                645                 650                 655

Pro Gly Pro Ala Gly Pro Gly Pro Gly Pro Gly Pro Gly Thr Ser
            660                 665                 670

Gly His Pro Gly Ser Pro Gly Ser Pro Gly Tyr Gln Gly Pro Pro Gly
        675                 680                 685

Glu Pro Gly Gln Ala Gly Pro Ser Gly Pro Gly Pro Gly Ala
    690                 695                 700

Ile Gly Pro Ser Gly Pro Ala Gly Lys Asp Gly Glu Ser Gly Arg Pro
705                 710                 715                 720

Gly Arg Pro Gly Glu Arg Gly Leu Pro Gly Pro Gly Ile Lys Gly
                725                 730                 735

Pro Ala Gly Ile Pro Gly Phe Pro Gly Met Lys Gly His Arg Gly Phe
            740                 745                 750
```

-continued

Asp Gly Arg Asn Gly Glu Lys Gly Glu Thr Gly Ala Pro Gly Leu Lys
    755                 760                 765
Gly Glu Asn Gly Leu Pro Glu Asn Gly Ala Pro Gly Pro Met Gly
        770                 775                 780
Pro Arg Gly Ala Pro Gly Glu Arg Gly Arg Pro Gly Leu Pro Gly Ala
785                 790                 795                 800
Ala Gly Ala Arg Gly Asn Asp Gly Ala Arg Gly Ser Asp Gly Gln Pro
            805                 810                 815
Gly Pro Pro Gly Pro Pro Gly Thr Ala Gly Phe Pro Gly Ser Pro Gly
            820                 825                 830
Ala Lys Gly Glu Val Gly Pro Ala Gly Ser Pro Gly Ser Asn Gly Ala
        835                 840                 845
Pro Gly Gln Arg Gly Glu Pro Gly Pro Gln Gly His Ala Gly Ala Gln
        850                 855                 860
Gly Pro Pro Gly Pro Pro Gly Ile Asn Gly Ser Pro Gly Gly Lys Gly
865                 870                 875                 880
Glu Met Gly Pro Ala Gly Ile Pro Gly Ala Pro Gly Leu Met Gly Ala
                885                 890                 895
Arg Gly Pro Pro Gly Pro Ala Gly Ala Asn Gly Ala Pro Gly Leu Arg
            900                 905                 910
Gly Gly Ala Gly Glu Pro Gly Lys Asn Gly Ala Lys Gly Glu Pro Gly
        915                 920                 925
Pro Arg Gly Glu Arg Gly Glu Ala Gly Ile Pro Gly Val Pro Gly Ala
        930                 935                 940
Lys Gly Glu Asp Gly Lys Asp Gly Ser Pro Gly Glu Pro Gly Ala Asn
945                 950                 955                 960
Gly Leu Pro Gly Ala Ala Gly Glu Arg Gly Ala Pro Gly Phe Arg Gly
            965                 970                 975
Pro Ala Gly Pro Asn Gly Ile Pro Gly Glu Lys Gly Pro Ala Gly Glu
            980                 985                 990
Arg Gly Ala Pro Gly Pro Ala Gly Pro Arg Gly Ala Ala Gly Glu Pro
        995                 1000                1005
Gly Arg Asp Gly Val Pro Gly Pro Gly Met Arg Gly Met Pro
        1010                1015                1020
Gly Ser Pro Gly Gly Pro Gly Ser Asp Gly Lys Pro Gly Pro Pro
        1025                1030                1035
Gly Ser Gln Gly Glu Ser Gly Arg Pro Gly Pro Pro Gly Pro Ser
        1040                1045                1050
Gly Pro Arg Gly Gln Pro Gly Val Met Gly Phe Pro Gly Pro Lys
        1055                1060                1065
Gly Asn Asp Gly Ala Pro Gly Lys Asn Gly Glu Arg Gly Gly Pro
        1070                1075                1080
Gly Gly Pro Gly Pro Gln Gly Pro Pro Gly Lys Asn Gly Glu Thr
        1085                1090                1095
Gly Pro Gln Gly Pro Pro Gly Pro Thr Gly Pro Gly Gly Asp Lys
        1100                1105                1110
Gly Asp Thr Gly Pro Pro Gly Pro Gln Gly Leu Gln Gly Leu Pro
        1115                1120                1125
Gly Thr Gly Gly Pro Pro Gly Glu Asn Gly Lys Pro Gly Glu Pro
        1130                1135                1140
Gly Pro Lys Gly Asp Ala Gly Ala Pro Gly Ala Pro Gly Gly Lys
        1145                1150                1155
Gly Asp Ala Gly Ala Pro Gly Glu Arg Gly Pro Pro Gly Leu Ala

-continued 1160              1165              1170

Gly Ala Pro Gly Leu Arg Gly Gly Ala Gly Pro Gly Pro Glu
        1175             1180             1185

Gly Gly Lys Gly Ala Ala Gly Pro Pro Gly Pro Gly Ala Ala
        1190             1195             1200

Gly Thr Pro Gly Leu Gln Gly Met Pro Gly Glu Arg Gly Gly Leu
        1205             1210             1215

Gly Ser Pro Gly Pro Lys Gly Asp Lys Gly Glu Pro Gly Gly Pro
        1220             1225             1230

Gly Ala Asp Gly Val Pro Gly Lys Asp Gly Pro Arg Gly Pro Thr
        1235             1240             1245

Gly Pro Ile Gly Pro Pro Gly Pro Ala Gly Gln Pro Gly Asp Lys
        1250             1255             1260

Gly Glu Gly Gly Ala Pro Gly Leu Pro Gly Ile Ala Gly Pro Arg
        1265             1270             1275

Gly Ser Pro Gly Glu Arg Gly Glu Thr Gly Pro Pro Gly Pro Ala
        1280             1285             1290

Gly Phe Pro Gly Ala Pro Gly Gln Asn Gly Glu Pro Gly Gly Lys
        1295             1300             1305

Gly Glu Arg Gly Ala Pro Gly Glu Lys Gly Glu Gly Gly Pro Pro
        1310             1315             1320

Gly Val Ala Gly Pro Pro Gly Gly Ser Gly Pro Ala Gly Pro Pro
        1325             1330             1335

Gly Pro Gln Gly Val Lys Gly Glu Arg Gly Ser Pro Gly Gly Pro
        1340             1345             1350

Gly Ala Ala Gly Phe Pro Gly Ala Arg Gly Leu Pro Gly Pro Pro
        1355             1360             1365

Gly Ser Asn Gly Asn Pro Gly Pro Pro Gly Pro Ser Gly Ser Pro
        1370             1375             1380

Gly Lys Asp Gly Pro Pro Gly Pro Ala Gly Asn Thr Gly Ala Pro
        1385             1390             1395

Gly Ser Pro Gly Val Ser Gly Pro Lys Gly Asp Ala Gly Gln Pro
        1400             1405             1410

Gly Glu Lys Gly Ser Pro Gly Ala Gln Gly Pro Pro Gly Ala Pro
        1415             1420             1425

Gly Pro Leu Gly Ile Ala Gly Ile Thr Gly Ala Arg Gly Leu Ala
        1430             1435             1440

Gly Pro Pro Gly Met Pro Gly Pro Arg Gly Ser Pro Gly Pro Gln
        1445             1450             1455

Gly Val Lys Gly Glu Ser Gly Lys Pro Gly Ala Asn Gly Leu Ser
        1460             1465             1470

Gly Glu Arg Gly Pro Pro Gly Pro Gln Gly Leu Pro Gly Leu Ala
        1475             1480             1485

Gly Thr Ala Gly Glu Pro Gly Arg Asp Gly Asn Pro Gly Ser Asp
        1490             1495             1500

Gly Leu Pro Gly Arg Asp Gly Ser Pro Gly Gly Lys Gly Asp Arg
        1505             1510             1515

Gly Glu Asn Gly Ser Pro Gly Ala Pro Gly Ala Pro Gly His Pro
        1520             1525             1530

Gly Pro Pro Gly Pro Val Gly Pro Ala Gly Lys Ser Gly Asp Arg
        1535             1540             1545

Gly Glu Ser Gly Pro Ala Gly Pro Ala Gly Ala Pro Gly Pro Ala
        1550             1555             1560

-continued

```
Gly Ser Arg Gly Ala Pro Gly Pro Gln Gly Pro Arg Gly Asp Lys
    1565            1570            1575

Gly Glu Thr Gly Glu Arg Gly Ala Ala Gly Ile Lys Gly His Arg
    1580            1585            1590

Gly Phe Pro Gly Asn Pro Gly Ala Pro Gly Ser Pro Gly Pro Ala
    1595            1600            1605

Gly Gln Gln Gly Ala Ile Gly Ser Pro Gly Pro Ala Gly Pro Arg
    1610            1615            1620

Gly Pro Val Gly Pro Ser Gly Pro Pro Gly Lys Asp Gly Thr Ser
    1625            1630            1635

Gly His Pro Gly Pro Ile Gly Pro Pro Gly Pro Arg Gly Asn Arg
    1640            1645            1650

Gly Glu Arg Gly Ser Glu Gly Ser Pro Gly His Pro Gly Gln Pro
    1655            1660            1665

Gly Pro Pro Gly Pro Pro Gly Ala Pro Gly Pro Cys Cys Gly Gly
    1670            1675            1680

Val Gly Ala Ala Ala Ile Ala Gly Ile Gly Gly Glu Lys Ala Gly
    1685            1690            1695

Gly Phe Ala Pro Tyr Tyr Gly Asp Glu Pro Met Asp Phe Lys Ile
    1700            1705            1710

Asn Thr Asp Glu Ile Met Thr Ser Leu Lys Ser Val Asn Gly Gln
    1715            1720            1725

Ile Glu Ser Leu Ile Ser Pro Asp Gly Ser Arg Lys Asn Pro Ala
    1730            1735            1740

Arg Asn Cys Arg Asp Leu Lys Phe Cys His Pro Glu Leu Lys Ser
    1745            1750            1755

Gly Glu Tyr Trp Val Asp Pro Asn Gln Gly Cys Lys Leu Asp Ala
    1760            1765            1770

Ile Lys Val Phe Cys Asn Met Glu Thr Gly Glu Thr Cys Ile Ser
    1775            1780            1785

Ala Asn Pro Leu Asn Val Pro Arg Lys His Trp Trp Thr Asp Ser
    1790            1795            1800

Ser Ala Glu Lys Lys His Val Trp Phe Gly Glu Ser Met Asp Gly
    1805            1810            1815

Gly Phe Gln Phe Ser Tyr Gly Asn Pro Glu Leu Pro Glu Asp Val
    1820            1825            1830

Leu Asp Val Gln Leu Ala Phe Leu Arg Leu Leu Ser Ser Arg Ala
    1835            1840            1845

Ser Gln Asn Ile Thr Tyr His Cys Lys Asn Ser Ile Ala Tyr Met
    1850            1855            1860

Asp Gln Ala Ser Gly Asn Val Lys Lys Ala Leu Lys Leu Met Gly
    1865            1870            1875

Ser Asn Glu Gly Glu Phe Lys Ala Glu Gly Asn Ser Lys Phe Thr
    1880            1885            1890

Tyr Thr Val Leu Glu Asp Gly Cys Thr Lys His Thr Gly Glu Trp
    1895            1900            1905

Ser Lys Thr Val Phe Glu Tyr Arg Thr Arg Lys Ala Val Arg Leu
    1910            1915            1920

Pro Ile Val Asp Ile Ala Pro Tyr Asp Ile Gly Gly Pro Asp Gln
    1925            1930            1935

Glu Phe Gly Val Asp Val Gly Pro Val Cys Phe Leu
    1940            1945            1950
```

<210> SEQ ID NO 11
<211> LENGTH: 37
<212> TYPE: DNA
<213> ORGANISM: Artificial Sequence
<220> FEATURE:
<223> OTHER INFORMATION: Oligonucleotide for PCR

<400> SEQUENCE: 11
gcttccagtc ttccgagcat gccaaaataa tagtggg    37

<210> SEQ ID NO 12
<211> LENGTH: 37
<212> TYPE: DNA
<213> ORGANISM: Artificial Sequence
<220> FEATURE:
<223> OTHER INFORMATION: Oligonucleotide for PCR

<400> SEQUENCE: 12
cccactatta ttttggcatg ctcggaagac tggaagc    37

<210> SEQ ID NO 13
<211> LENGTH: 4815
<212> TYPE: DNA
<213> ORGANISM: Artificial Sequence
<220> FEATURE:
<223> OTHER INFORMATION: DNA molecule based on procollagen type III
    N-propeptide. Sequence prior to N100 replaced with the sequence
    for the G3 domain of the alpha3 chain of laminin-5 whilst
    retaining the collagen III signal sequence.

<400> SEQUENCE: 13
atgatgagct tgtgcaaaa ggggagctgg ctacttctcg ctctgcttca tcccactatt    60
attttggcat gctcggaaga ctggaagctt gtgcgatctg cctcattctc cagaggagga   120
caattgagtt tcactgattt gggcttacca cctactgacc acctccaggc tcatttgga   180 tttcagacct ttcaacccag tggcatatta ttagatcatc agacatggac aaggaacctg   240
caggtcactc tggaagatgg ttacattgaa ttgagcacca gcgatagcgg cggcccaatt   300
tttaaatctc cacagacgta tatggatggt ttactgcatt atgtatctgt aataagcgac   360
aactctggac tacggcttct catcgatgac cagcttctga aaatagcaa aaggctaaaa   420 cacatttcaa gttcccggca gtctctgcgt ctgggcggga gcaattttga gggttgtatt   480
agcaatgttt ttgtccagag gttatcactg agtcctgaag tcctagattt gaccagtaac   540
tctctcaaga gagatgtgtc cctgggaggc tgcagtttaa acaaaccacc ttttctaatg   600
ttgcttaaag gttctaccag gtttaacaag accaagactt ttcgtatcaa ccagctgttg   660
caggacacac cagtggcctc cccaaggagc gtgaaggtgt ggcaagatgc taatggtcaa   720
ggacctcaag gccccaaggg agatccaggc cctcctggta ttcctgggag aaatggtgac   780
cctggtattc caggacaacc agggtcccct ggttctcctg gccccctgg aatctgtgaa   840 tcatgcccta ctggtcctca gaactattct ccccagtatg attcatatga tgtcaagtct   900
ggagtagcag taggaggact cgcaggctat cctggaccag ctggccccc aggccctccc   960 ggtccccctg gtacatctgg tcatcctggt tcccctggat ctccaggata ccaaggaccc  1020
cctggtgaac ctgggcaagc tggtccttca ggccctccag acctcctgg tgctataggt  1080 ccatctggtc ctgctggaaa agatggagaa tcaggtagac ccggacgacc tggagagcga  1140
ggattgcctg gacctccagg tatcaaaggt ccagctggga tacctggatt ccctggtatg  1200
aaaggacaca gaggcttcga tggacgaaat ggagaaaagg gtgaaacagg tgctcctgga  1260

-continued

```
ttaaagggtg aaaatggtct tccaggcgaa aatggagctc ctggacccat gggtccaaga    1320
ggggctcctg gtgagcgagg acggccagga cttcctgggg ctgcaggtgc tcggggtaat    1380
gacggtgctc gaggcagtga tggtcaacca ggccctcctg gtcctcctgg aactgccgga    1440
ttccctggat cccctggtgc taagggtgaa gttggacctg cagggtctcc tggttcaaat    1500
ggtgcccctg gacaaagagg agaacctgga cctcagggac acgctggtgc tcaaggtcct    1560
cctggccctc ctgggattaa tggtagtcct ggtggtaaag gcgaaatggg tcccgctggc    1620
attcctggag ctcctggact gatgggagcc cggggtcctc caggaccagc cggtgctaat    1680
ggtgctcctg gactgcgagg tggtgcaggt gagcctggta agaatggtgc caaaggagag    1740
cccggaccac gtggtgaacg cggtgaggct ggtattccag gtgttccagg agctaaaggc    1800
gaagatggca aggatggatc acctggagaa cctggtgcaa atgggcttcc aggagctgca    1860
ggagaaaggg gtgcccctgg gttccgagga cctgctggac aaatggcat cccaggagaa    1920
aagggtcctg ctggagagcg tggtgctcca ggccctgcag gcccagagg agctgctgga    1980
gaacctggca gagatggcgt ccctggaggt ccaggaatga ggggcatgcc cggaagtcca    2040
ggaggaccag aagtgatgg gaaaccaggg cctcccggaa gtcaaggaga aagtggtcga    2100
ccaggtcctc ctgggccatc tggtccccga ggtcagcctg gtgtcatggg cttccccggt    2160
cctaaaggaa atgatggtgc tcctggtaag aatggagaac gaggtggccc tggaggacct    2220
ggccctcagg gtcctcctgg aaagaatggt gaaactggac ctcaaggacc cccagggcct    2280
actgggcctg gtgtgacaa aggagacaca ggaccccctg gtccacaagg attacaaggc    2340
ttgcctggta caggtggtcc tccaggagaa aatggaaaac tggggaacc aggtccaaag    2400
ggtgatgccg gtgcacctgg agctccagga ggcaagggtg atgctggtgc ccctggtgaa    2460
cgtggacctc ctggattggc aggggcccca ggacttagag gtggagctgg tccccctggt    2520
cccgaaggag gaaagggtgc tgctggtcct cctgggccac ctggtgctgc tggtactcct    2580
ggtctgcaag aatgcctgg agaaagagga ggtcttggaa gtcctggtcc aaagggtgac    2640
aagggtgaac caggcggccc aggtgctgat ggtgtcccag gaaagatgg cccaagggt    2700
cctactggtc ctattggtcc tcctggccca gctggccagc ctggagataa gggtgaaggt    2760
ggtgccccg acttccagg tatagctgga cctcgtggta gcctggtga gagaggtgaa    2820
actggccctc aggacctgc tggtttccct ggtgctcctg gacagaatgg tgaacctggt    2880
ggtaaaggag aaagagggc tccgggtgag aaaggtgaag gaggccctcc tggagttgca    2940
ggaccccctg gaggttctgg acctgctggt cctcctggtc cccaaggtgt caaggtgaa    3000
cgtggcagtc ctggtggacc tggtgctgct ggcttccctg gtgctcgtgg tcttcctggt    3060
cctcctggta gtaatggtaa cccaggaccc ccaggtccca cgggttctcc aggcaaggat    3120
gggcccccag gtcctgcggg taacactggt gctcctggca gccctggagt gtctggacca    3180
aaaggtgatg ctggccaacc aggagagaag ggatcgcctg gtgcccaggg cccaccagga    3240
gctccaggcc cacttgggat tgctgggatc actggagcac ggggtcttgc aggaccacca    3300
ggcatgccag gtcctagggg aagccctggc cctcagggtc taagggtga agtgggaaa    3360
ccaggagcta acggtctcag tggagaacgt ggtccccctg gaccccaggg tcttcctggt    3420
ctggctggta cagctggtga acctggaaga gatggaaacc ctggatcaga tggtcttcca    3480
ggccgagatg gatctcctgg tggcaagggt gatcgtggtg aaaatggctc tcctggtgcc    3540
cctggcgctc ctggtcatcc aggcccacct ggtcctgtcg gtccagctgg aaagagtggt    3600
gacagaggag aaagtggccc tgctggccct gctggtgctc ccggtcctgc tggttcccga    3660
```

-continued

```
ggtgctcctg gtcctcaagg cccacgtggt gacaaaggtg aaacaggtga acgtggagct    3720
gctggcatca aggacatcg aggattccct ggtaatccag gtgccccagg ttctccaggc    3780
cctgctggtc agcagggtgc aatcggcagt ccaggacctg caggcccag aggacctgtt    3840
ggacccagtg gacctcctgg caaagatgga accagtggac atccaggtcc cattggacca    3900
ccagggcctc gaggtaacag aggtgaaaga ggatctgagg gctccccagg ccacccaggg    3960
caaccaggcc ctcctggacc tcctggtgcc cctggtcctt gctgtggtgg tgttggagcc    4020
gctgccattg ctgggattgg aggtgaaaaa gctggcggtt ttgccccgta ttatggagat    4080
gaaccaatgg atttcaaaat caacaccgat gagattatga cttcactcaa gtctgttaat    4140
ggacaaatag aaagcctcat tagtcctgat ggttctcgta aaaacccgc tagaaactgc    4200
agagacctga attctgcca tcctgaactc aagagtggag aatactgggt tgaccctaac    4260
caaggatgca aattggatgc tatcaaggta ttctgtaata tggaaactgg ggaaacatgc    4320
ataagtgcca atcctttgaa tgttccacgg aaacactggt ggacagattc tagtgctgag    4380
aagaaacacg tttggtttgg agagtccatg gatggtggtt ttcagtttag ctacggcaat    4440
cctgaacttc ctgaagatgt ccttgatgtg cagctggcat tccttcgact tctctccagc    4500
cgagcttccc agaacatcac atatcactgc aaaaatagca ttgcatacat ggatcaggcc    4560
agtggaaatg taagaaggc cctgaagctg atggggtcaa atgaaggtga attcaaggct    4620
gaaggaaata gcaaattcac ctacacagtt ctggaggatg gttgcacgaa acacactggg    4680
gaatggagca aaacagtctt tgaatatcga acacgcaagg ctgtgagact acctattgta    4740
gatattgcac cctatgacat tggtggtcct gatcaagaat ttggtgtgga cgttggccct    4800
gtttgctttt tataa                                                    4815
```

<210> SEQ ID NO 14
<211> LENGTH: 1604
<212> TYPE: PRT
<213> ORGANISM: Artificial Sequence
<220> FEATURE:
<223> OTHER INFORMATION: Sequence of modified pro-alpha chain.

<400> SEQUENCE: 14

```
Met Met Ser Phe Val Gln Lys Gly Ser Trp Leu Leu Leu Ala Leu Leu
1               5                   10                  15

His Pro Thr Ile Ile Leu Ala Cys Ser Glu Asp Trp Lys Leu Val Arg
            20                  25                  30

Ser Ala Ser Phe Ser Arg Gly Gly Gln Leu Ser Phe Thr Asp Leu Gly
        35                  40                  45

Leu Pro Pro Thr Asp His Leu Gln Ala Ser Phe Gly Phe Gln Thr Phe
    50                  55                  60

Gln Pro Ser Gly Ile Leu Leu Asp His Gln Thr Trp Thr Arg Asn Leu
65                  70                  75                  80

Gln Val Thr Leu Glu Asp Gly Tyr Ile Glu Leu Ser Thr Ser Asp Ser
                85                  90                  95

Gly Gly Pro Ile Phe Lys Ser Pro Gln Thr Tyr Met Asp Gly Leu Leu
            100                 105                 110

His Tyr Val Ser Val Ile Ser Asp Asn Ser Gly Leu Arg Leu Leu Ile
        115                 120                 125

Asp Asp Gln Leu Leu Arg Asn Ser Lys Arg Leu Lys His Ile Ser Ser
    130                 135                 140

Ser Arg Gln Ser Leu Arg Leu Gly Gly Ser Asn Phe Glu Gly Cys Ile
```

```
                    145                 150                 155                 160
            Ser Asn Val Phe Val Gln Arg Leu Ser Leu Ser Pro Glu Val Leu Asp
                            165                 170                 175

Leu Thr Ser Asn Ser Leu Lys Arg Asp Val Ser Leu Gly Gly Cys Ser
                        180                 185                 190

Leu Asn Lys Pro Pro Phe Leu Met Leu Leu Lys Gly Ser Thr Arg Phe
                        195                 200                 205

Asn Lys Thr Lys Thr Phe Arg Ile Asn Gln Leu Leu Gln Asp Thr Pro
                    210                 215                 220

Val Ala Ser Pro Arg Ser Val Lys Val Trp Gln Asp Ala Asn Gly Gln
            225                 230                 235                 240

Gly Pro Gln Gly Pro Lys Gly Asp Pro Gly Pro Gly Ile Pro Gly
                            245                 250                 255

Arg Asn Gly Asp Pro Gly Ile Pro Gly Gln Pro Gly Ser Pro Gly Ser
                        260                 265                 270

Pro Gly Pro Pro Gly Ile Cys Glu Ser Cys Pro Thr Gly Pro Gln Asn
                        275                 280                 285

Tyr Ser Pro Gln Tyr Asp Ser Tyr Asp Val Lys Ser Gly Val Ala Val
                    290                 295                 300

Gly Gly Leu Ala Gly Tyr Pro Gly Pro Ala Gly Pro Pro Gly Pro Pro
            305                 310                 315                 320

Gly Pro Pro Gly Thr Ser Gly His Pro Gly Ser Pro Gly Ser Pro Gly
                            325                 330                 335

Tyr Gln Gly Pro Pro Gly Glu Pro Gly Gln Ala Gly Pro Ser Gly Pro
                        340                 345                 350

Pro Gly Pro Pro Gly Ala Ile Gly Pro Ser Gly Pro Ala Gly Lys Asp
                        355                 360                 365

Gly Glu Ser Gly Arg Pro Gly Arg Pro Gly Glu Arg Gly Leu Pro Gly
                    370                 375                 380

Pro Pro Gly Ile Lys Gly Pro Ala Gly Ile Pro Gly Phe Pro Gly Met
            385                 390                 395                 400

Lys Gly His Arg Gly Phe Asp Gly Arg Asn Gly Glu Lys Gly Glu Thr
                            405                 410                 415

Gly Ala Pro Gly Leu Lys Gly Glu Asn Gly Leu Pro Gly Glu Asn Gly
                        420                 425                 430

Ala Pro Gly Pro Met Gly Pro Arg Gly Ala Pro Gly Glu Arg Gly Arg
                        435                 440                 445

Pro Gly Leu Pro Gly Ala Ala Gly Ala Arg Gly Asn Asp Gly Ala Arg
                    450                 455                 460

Gly Ser Asp Gly Gln Pro Gly Pro Pro Gly Pro Pro Gly Thr Ala Gly
            465                 470                 475                 480

Phe Pro Gly Ser Pro Gly Ala Lys Gly Glu Val Gly Pro Ala Gly Ser
                            485                 490                 495

Pro Gly Ser Asn Gly Ala Pro Gly Gln Arg Gly Glu Pro Gly Pro Gln
                        500                 505                 510

Gly His Ala Gly Ala Gln Gly Pro Pro Gly Pro Pro Gly Ile Asn Gly
                        515                 520                 525

Ser Pro Gly Gly Lys Gly Glu Met Gly Pro Ala Gly Ile Pro Gly Ala
                    530                 535                 540

Pro Gly Leu Met Gly Ala Arg Gly Pro Pro Gly Pro Ala Gly Ala Asn
            545                 550                 555                 560

Gly Ala Pro Gly Leu Arg Gly Gly Ala Gly Glu Pro Gly Lys Asn Gly
                            565                 570                 575
```

-continued

```
Ala Lys Gly Glu Pro Gly Pro Arg Gly Glu Arg Gly Glu Ala Gly Ile
            580                 585                 590
Pro Gly Val Pro Gly Ala Lys Gly Glu Asp Gly Lys Asp Gly Ser Pro
            595                 600                 605
Gly Glu Pro Gly Ala Asn Gly Leu Pro Gly Ala Ala Gly Glu Arg Gly
            610                 615                 620
Ala Pro Gly Phe Arg Gly Pro Ala Gly Pro Asn Gly Ile Pro Gly Glu
625                 630                 635                 640
Lys Gly Pro Ala Gly Glu Arg Gly Ala Pro Gly Pro Ala Gly Pro Arg
            645                 650                 655
Gly Ala Ala Gly Glu Pro Gly Arg Asp Gly Val Pro Gly Gly Pro Gly
            660                 665                 670
Met Arg Gly Met Pro Gly Ser Pro Gly Gly Pro Gly Ser Asp Gly Lys
            675                 680                 685
Pro Gly Pro Pro Gly Ser Gln Gly Glu Ser Gly Arg Pro Gly Pro Pro
            690                 695                 700
Gly Pro Ser Gly Pro Arg Gly Gln Pro Gly Val Met Gly Phe Pro Gly
705                 710                 715                 720
Pro Lys Gly Asn Asp Gly Ala Pro Gly Lys Asn Gly Glu Arg Gly Gly
            725                 730                 735
Pro Gly Gly Pro Gly Pro Gln Gly Pro Gly Lys Asn Gly Glu Thr
            740                 745                 750
Gly Pro Gln Gly Pro Pro Gly Pro Thr Gly Pro Gly Gly Asp Lys Gly
            755                 760                 765
Asp Thr Gly Pro Pro Gly Pro Gln Gly Leu Gln Gly Leu Pro Gly Thr
770                 775                 780
Gly Gly Pro Pro Gly Glu Asn Gly Lys Pro Gly Glu Pro Gly Pro Lys
785                 790                 795                 800
Gly Asp Ala Gly Ala Pro Gly Ala Pro Gly Gly Lys Gly Asp Ala Gly
            805                 810                 815
Ala Pro Gly Glu Arg Gly Pro Pro Gly Leu Ala Gly Ala Pro Gly Leu
            820                 825                 830
Arg Gly Gly Ala Gly Pro Pro Gly Pro Glu Gly Gly Lys Gly Ala Ala
            835                 840                 845
Gly Pro Pro Gly Pro Pro Gly Ala Ala Gly Thr Pro Gly Leu Gln Gly
            850                 855                 860
Met Pro Gly Glu Arg Gly Gly Leu Gly Ser Pro Gly Pro Lys Gly Asp
865                 870                 875                 880
Lys Gly Glu Pro Gly Gly Pro Gly Ala Asp Gly Val Pro Gly Lys Asp
            885                 890                 895
Gly Pro Arg Gly Pro Thr Gly Pro Ile Gly Pro Pro Gly Pro Ala Gly
            900                 905                 910
Gln Pro Gly Asp Lys Gly Glu Gly Gly Ala Pro Gly Leu Pro Gly Ile
            915                 920                 925
Ala Gly Pro Arg Gly Ser Pro Gly Glu Arg Gly Glu Thr Gly Pro Pro
            930                 935                 940
Gly Pro Ala Gly Phe Pro Gly Ala Pro Gly Gln Asn Gly Glu Pro Gly
945                 950                 955                 960
Gly Lys Gly Glu Arg Gly Ala Pro Gly Glu Lys Gly Glu Gly Gly Pro
            965                 970                 975
Pro Gly Val Ala Gly Pro Pro Gly Gly Ser Gly Pro Ala Gly Pro Pro
            980                 985                 990
```

```
Gly Pro Gln Gly Val Lys Gly Glu Arg Gly Ser Pro Gly Gly Pro Gly
        995                 1000                1005

Ala Ala Gly Phe Pro Gly Ala Arg Gly Leu Pro Gly Pro Pro Gly
    1010                1015                1020

Ser Asn Gly Asn Pro Gly Pro Pro Gly Pro Ser Gly Ser Pro Gly
    1025                1030                1035

Lys Asp Gly Pro Pro Gly Pro Ala Gly Asn Thr Gly Ala Pro Gly
    1040                1045                1050

Ser Pro Gly Val Ser Gly Pro Lys Gly Asp Ala Gly Gln Pro Gly
    1055                1060                1065

Glu Lys Gly Ser Pro Gly Ala Gln Gly Pro Pro Gly Ala Pro Gly
    1070                1075                1080

Pro Leu Gly Ile Ala Gly Ile Thr Gly Ala Arg Gly Leu Ala Gly
    1085                1090                1095

Pro Pro Gly Met Pro Gly Pro Arg Gly Ser Pro Gly Pro Gln Gly
    1100                1105                1110

Val Lys Gly Glu Ser Gly Lys Pro Gly Ala Asn Gly Leu Ser Gly
    1115                1120                1125

Glu Arg Gly Pro Pro Gly Pro Gln Gly Leu Pro Gly Leu Ala Gly
    1130                1135                1140

Thr Ala Gly Glu Pro Gly Arg Asp Gly Asn Pro Gly Ser Asp Gly
    1145                1150                1155

Leu Pro Gly Arg Asp Gly Ser Pro Gly Gly Lys Gly Asp Arg Gly
    1160                1165                1170

Glu Asn Gly Ser Pro Gly Ala Pro Gly Ala Pro Gly His Pro Gly
    1175                1180                1185

Pro Pro Gly Pro Val Gly Pro Ala Gly Lys Ser Gly Asp Arg Gly
    1190                1195                1200

Glu Ser Gly Pro Ala Gly Pro Ala Gly Ala Pro Gly Pro Ala Gly
    1205                1210                1215

Ser Arg Gly Ala Pro Gly Pro Gln Gly Pro Arg Gly Asp Lys Gly
    1220                1225                1230

Glu Thr Gly Glu Arg Gly Ala Ala Gly Ile Lys Gly His Arg Gly
    1235                1240                1245

Phe Pro Gly Asn Pro Gly Ala Pro Gly Ser Pro Gly Pro Ala Gly
    1250                1255                1260

Gln Gln Gly Ala Ile Gly Ser Pro Gly Pro Ala Gly Pro Arg Gly
    1265                1270                1275

Pro Val Gly Pro Ser Gly Pro Pro Gly Lys Asp Gly Thr Ser Gly
    1280                1285                1290

His Pro Gly Pro Ile Gly Pro Pro Gly Pro Arg Gly Asn Arg Gly
    1295                1300                1305

Glu Arg Gly Ser Glu Gly Ser Pro Gly His Pro Gly Gln Pro Gly
    1310                1315                1320

Pro Pro Gly Pro Pro Gly Ala Pro Gly Pro Cys Cys Gly Gly Val
    1325                1330                1335

Gly Ala Ala Ala Ile Ala Gly Ile Gly Gly Glu Lys Ala Gly Gly
    1340                1345                1350

Phe Ala Pro Tyr Tyr Gly Asp Glu Pro Met Asp Phe Lys Ile Asn
    1355                1360                1365

Thr Asp Glu Ile Met Thr Ser Leu Lys Ser Val Asn Gly Gln Ile
    1370                1375                1380

Glu Ser Leu Ile Ser Pro Asp Gly Ser Arg Lys Asn Pro Ala Arg
```

-continued

```
           1385                1390                1395

Asn Cys Arg Asp Leu Lys Phe Cys His Pro Glu Leu Lys Ser Gly
        1400                1405                1410

Glu Tyr Trp Val Asp Pro Asn Gln Gly Cys Lys Leu Asp Ala Ile
    1415                1420                1425

Lys Val Phe Cys Asn Met Glu Thr Gly Glu Thr Cys Ile Ser Ala
1430                1435                1440

Asn Pro Leu Asn Val Pro Arg Lys His Trp Trp Thr Asp Ser Ser
        1445                1450                1455

Ala Glu Lys Lys His Val Trp Phe Gly Glu Ser Met Asp Gly Gly
    1460                1465                1470

Phe Gln Phe Ser Tyr Gly Asn Pro Glu Leu Pro Glu Asp Val Leu
1475                1480                1485

Asp Val Gln Leu Ala Phe Leu Arg Leu Leu Ser Ser Arg Ala Ser
        1490                1495                1500

Gln Asn Ile Thr Tyr His Cys Lys Asn Ser Ile Ala Tyr Met Asp
    1505                1510                1515

Gln Ala Ser Gly Asn Val Lys Lys Ala Leu Lys Leu Met Gly Ser
1520                1525                1530

Asn Glu Gly Glu Phe Lys Ala Glu Gly Asn Ser Lys Phe Thr Tyr
        1535                1540                1545

Thr Val Leu Glu Asp Gly Cys Thr Lys His Thr Gly Glu Trp Ser
    1550                1555                1560

Lys Thr Val Phe Glu Tyr Arg Thr Arg Lys Ala Val Arg Leu Pro
1565                1570                1575

Ile Val Asp Ile Ala Pro Tyr Asp Ile Gly Gly Pro Asp Gln Glu
        1580                1585                1590

Phe Gly Val Asp Val Gly Pro Val Cys Phe Leu
    1595                1600
```

<210> SEQ ID NO 15
<211> LENGTH: 37
<212> TYPE: DNA
<213> ORGANISM: Artificial Sequence
<220> FEATURE:
<223> OTHER INFORMATION: PCR primer

<400> SEQUENCE: 15
cttgtagatg cggccgcatg aagtccagcg gcctctt            37

<210> SEQ ID NO 16
<211> LENGTH: 30
<212> TYPE: DNA
<213> ORGANISM: Artificial Sequence
<220> FEATURE:
<223> OTHER INFORMATION: PCR primer

<400> SEQUENCE: 16
cttcaacagc agctttcaca ggggaaacgc                    30

<210> SEQ ID NO 17
<211> LENGTH: 30
<212> TYPE: DNA
<213> ORGANISM: Artificial Sequence
<220> FEATURE:
<223> OTHER INFORMATION: PCR primer

<400> SEQUENCE: 17
tgtgaaagct gctgttgaag gaggatgttc                    30

<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18
ggacctggtc gaccactttc                                                  20

<210> SEQ ID NO 19
<211> LENGTH: 22
<212> TYPE: DNA
<213> ORGANISM: Artificial Sequence
<220> FEATURE:
<223> OTHER INFORMATION: PCR primer

<400> SEQUENCE: 19
gtaatacgac tcactatagg gc                                               22

<210> SEQ ID NO 20
<211> LENGTH: 18
<212> TYPE: DNA
<213> ORGANISM: Artificial Sequence
<220> FEATURE:
<223> OTHER INFORMATION: PCR primer

<400> SEQUENCE: 20
gctgttgaag gaggatgt                                                    18

<210> SEQ ID NO 21
<211> LENGTH: 18
<212> TYPE: DNA
<213> ORGANISM: Artificial Sequence
<220> FEATURE:
<223> OTHER INFORMATION: PCR primer

<400> SEQUENCE: 21
agaggcttcg atggacga                                                    18

<210> SEQ ID NO 22
<211> LENGTH: 18
<212> TYPE: DNA
<213> ORGANISM: Artificial Sequence
<220> FEATURE:
<223> OTHER INFORMATION: PCR primer

<400> SEQUENCE: 22
ggactgcgag gtggtgca                                                    18

<210> SEQ ID NO 23
<211> LENGTH: 18
<212> TYPE: DNA
<213> ORGANISM: Artificial Sequence
<220> FEATURE:
<223> OTHER INFORMATION: PCR primer

<400> SEQUENCE: 23
ttctcccagg aataccag                                                    18

<210> SEQ ID NO 24
<211> LENGTH: 18
<212> TYPE: DNA
<213> ORGANISM: Artificial Sequence
<220> FEATURE:

<223> OTHER INFORMATION: PCR primer

<400> SEQUENCE: 24
agggaatccg gcagttcc                                                 18

<210> SEQ ID NO 25
<211> LENGTH: 18
<212> TYPE: DNA
<213> ORGANISM: Artificial Sequence
<220> FEATURE:
<223> OTHER INFORMATION: PCR primer

<400> SEQUENCE: 25
ctcggggacc agatggcc                                                 18

<210> SEQ ID NO 26
<211> LENGTH: 4719
<212> TYPE: DNA
<213> ORGANISM: Artificial Sequence
<220> FEATURE:
<223> OTHER INFORMATION: DNA molecule based on procollagen type III
      N-propeptide. Procollagen type III N-propeptide sequence replaced
      with the sequence for SLPI whilst retaining the collagen III
      signal sequence.

<400> SEQUENCE: 26
atgaagtcca gcggcctctt cccctccctg gtgctgcttg ccctgggaac tctggcacct     60
tgggctgtgg aaggctctgg aaagtccttc aaagctggag tctgtcctcc taagaaatct    120
gcccagtgcc ttagatacaa gaaacctgag tgccagagtg actggcagtg tccagggaag    180
aagagatgtt gtcctgacac ttgtggcatc aaatgcctgg atcctgttga cacccccaaac   240 ccaacaagga ggaagcctgg gaagtgccca gtgacttatg ccaatgtttt gatgcttaac    300
ccccccaatt tctgtgagat ggatggccag tgcaagcgtg acttgaagtg ttgcatgggc    360
atgtgtggga atcctgcgt ttcccctgtg aaagctgctg ttgaaggagg atgttcccat     420
cttggtcagt cctatgcgga tagagatgtc tggaagccag aaccatgcca atatgtgtc    480 tgtgactcag gatccgttct ctgcgatgac ataatatgtg acgatcaaga attagactgc    540
cccaacccag aaattccatt ggagaatgt tgtgcagttt gcccacagcc tccaactgct     600
cctactcgcc tcctaatgg tcaaggacct caaggcccca agggagatcc aggccctcct    660
ggtattcctg ggagaaatgg tgaccctggt attccaggac aaccagggtc ccctggttct    720 cctggcccc ctggaatctg tgaatcatgc cctactggtc ctcagaacta ttctccccag     780
tatgattcat atgatgtcaa gtctggagta gcagtaggag gactcgcagg ctatcctgga    840
ccagctggcc cccaggccc tccggtccc ctggtacat ctggtcatcc tggttccccct     900 ggatctccag ataccaagg accccctggt gaacctgggc aagctggtcc ttcaggccct   960
ccaggacctc ctggtgctat aggtccatct ggtcctgctg gaaagatgg agaatcaggt    1020 agacccggac gacctggaga gcgaggatctg cctggacctc aggtatcaa aggtccagct    1080 gggatacctg gattccctgg tatgaaagga cacagaggct tcgatggacg aaatggagaa    1140
aagggtgaaa caggtgctcc tggattaaag ggtgaaaatg gtcttccagg cgaaaatgga    1200
gctcctggac ccatgggtcc aagaggggct cctggtgagc gaggacggcc aggacttcct    1260
ggggctgcag gtgctcgggg taatgacggt gctcgaggca tgatggtca accaggccct    1320 cctggtcctc ctggaactgc cggattccct ggatcccctg gtgctaaggg tgaagttgga    1380
cctgcagggt ctcctggttc aaatggtgcc cctggacaaa gaggagaacc tggacctcag    1440

```
ggacacgctg gtgctcaagg tcctcctggc cctcctggga ttaatggtag tcctggtggt    1500
aaaggcgaaa tgggtcccgc tggcattcct ggagctcctg gactgatggg agcccggggt    1560
cctccaggac cagccggtgc taatggtgct cctggactgc gaggtggtgc aggtgagcct    1620
ggtaagaatg gtgccaaagg agagcccgga ccacgtggtg aacgcggtga ggctggtatt    1680
ccaggtgttc caggagctaa aggcgaagat ggcaaggatg gatcacctgg agaacctggt    1740
gcaaatgggc ttccaggagc tgcaggagaa aggggtgccc ctgggttccg aggacctgct    1800
ggaccaaatg gcatcccagg agaaaagggt cctgctggag agcgtggtgc tccaggccct    1860
gcagggccca ggagagctgc tggagaacct ggcagagatg gcgtccctgg aggtccagga    1920
atgaggggca tgcccggaag tccaggagga ccaggaagtg atgggaaacc agggcctccc    1980
ggaagtcaag gagaaagtgg tcgaccaggt cctcctgggc catctggtcc ccagggtcag    2040
cctggtgtca tgggcttccc cggtcctaaa ggaaatgatg gtgctcctgg taagaatgga    2100
gaacgaggtg gccctggagg acctggccct caggtcctc ctggaaagaa tggtgaaact    2160
ggacctcaag acccccagg gcctactggg cctggtggtg acaaaggaga cacaggaccc    2220
cctggtccac aaggattaca aggcttgcct ggtacaggtg gtcctccagg agaaaatgga    2280
aaacctgggg aaccaggtcc aaagggtgat gccggtgcac ctggagctcc aggaggcaag    2340
ggtgatgctg gtgcccctgg tgaacgtgga cctcctggat tggcagggc cccaggactt    2400 agaggtggag ctggtcccc tggtcccgaa ggaggaaagg gtgctgctgg tcctcctggg    2460
ccacctggtc tgctggtac tcctggtctg caaggaatgc ctggagaaag gaggagtctt    2520
ggaagtcctg gtccaaaggg tgacaagggt gaaccaggcg gcccaggtgc tgatggtgtc    2580
ccagggaaag atggcccaag gggtcctact ggtcctattg gtcctcctgg cccagctggc    2640
cagcctggag ataagggtga aggtggtgcc cccggacttc caggtatagc tggacctcgt    2700
ggtagccctg gtgagagagg tgaaactggc cctccaggac tgctggtttt ccctggtgct    2760
cctggacaga atggtgaacc tggtggtaaa ggagaaagag gggctccggg tgagaaaggt    2820
gaaggaggcc ctcctggagt tgcaggacct cctggaggtt ctggacctgc tggtcctcct    2880 ggtcccccaag gtgtcaaagg tgaacgtggc agtcctggtg gacctggtgc tgctggcttc    2940
cctggtgctc gtggtcttcc tggtcctcct ggtagtaatg gtaacccagg accccccaggt    3000 cccagcggtt ctccaggcaa ggatgggccc ccaggtcctg cgggtaacac tggtgctcct    3060
ggcagccctg gagtgtctgg accaaaaggt gatgctggcc aaccaggaga gaagggatcg    3120
cctggtgccc agggcccacc aggagctcca ggcccacttg ggattgctgg gatcactgga    3180
gcacggggtc ttgcaggacc accaggcatg ccaggtccta ggggaagccc tggccctcag    3240
ggtgtcaagg gtgaaagtgg gaaaccagga gctaacggtc tcagtggaga acgtggtccc    3300
cctggacccc agggtcttcc tggtctggct ggtacagctg gtgaacctgg aagagatgga    3360
aaccctggat cagatggtct tccaggccga gatggatctc ctggtggcaa gggtgatcgt    3420
ggtgaaaatg gctctcctgg tgcccctggc gctcctggtc atccaggccc acctggtcct    3480
gtcggtccag ctggaaagag tggtgacaga ggagaaagtg gccctgctgg ccctgctggt    3540
gctcccggtc ctgctggttc cgaggtgctc ctggtcctc aaggcccacg tggtgacaaa    3600
ggtgaaacag gtgaacgtgg agctgctggc atcaaaggac atcgaggatt ccctggtaat    3660
ccaggtgccc caggttctcc aggccctgct ggtcagcagg gtgcaatcgg cagtccagga    3720
cctgcaggcc ccagaggacc tgttggaccc agtggacctc ctgcaaaaga tggaaccagt    3780
ggacatccag gtcccattgg accaccaggg cctcgaggta acagaggtga aagaggatct    3840
```

```
gagggctccc caggccaccc agggcaacca ggccctcctg gacctcctgg tgcccctggt    3900
ccttgctgtg gtggtgttgg agccgctgcc attgctggga ttggaggtga aaaagctggc    3960
ggttttgccc cgtattatgg agatgaacca atggatttca aaatcaacac cgatgagatt    4020
atgacttcac tcaagtctgt taatggacaa atagaaagcc tcattagtcc tgatggttct    4080
cgtaaaaacc ccgctagaaa ctgcagagac ctgaaattct gccatcctga actcaagagt    4140
ggagaatact gggttgaccc taaccaagga tgcaaattgg atgctatcaa ggtattctgt    4200
aatatggaaa ctggggaaac atgcataagt gccaatcctt tgaatgttcc acggaaacac    4260
tggtggacag attctagtgc tgagaagaaa cacgtttggt ttggagagtc catggatggt    4320
ggttttcagt ttagctacgg caatcctgaa cttcctgaag atgtccttga tgtgcagctg    4380
gcattccttc gacttctctc cagccgagct tcccagaaca tcacatatca ctgcaaaaat    4440
agcattgcat acatggatca ggccagtgga aatgtaaaga aggccctgaa gctgatgggg    4500
tcaaatgaag gtgaattcaa ggctgaagga aatagcaaat tcacctacac agttctggag    4560
gatggttgca cgaaacacac tggggaatgg agcaaaacag tctttgaata tcgaacacgc    4620
aaggctgtga gactacctat tgtagatatt gcaccctatg acattggtgg tcctgatcaa    4680
gaatttggtg tggacgttgg ccctgtttgc ttttttataa                          4719
```

```
<210> SEQ ID NO 27
<211> LENGTH: 1572
<212> TYPE: PRT
<213> ORGANISM: Artificial Sequence
<220> FEATURE:
<223> OTHER INFORMATION: Sequence of modified pro-alpha chain.

<400> SEQUENCE: 27

Met Lys Ser Ser Gly Leu Phe Pro Phe Leu Val Leu Leu Ala Leu Gly
1               5                   10                  15

Thr Leu Ala Pro Trp Ala Val Glu Gly Ser Gly Lys Ser Phe Lys Ala
            20                  25                  30

Gly Val Cys Pro Pro Lys Lys Ser Ala Gln Cys Leu Arg Tyr Lys Lys
        35                  40                  45

Pro Glu Cys Gln Ser Asp Trp Gln Cys Pro Gly Lys Lys Arg Cys Cys
    50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys
                85                  90                  95

Leu Met Leu Asn Pro Pro Asn Phe Cys Glu Met Asp Gly Gln Cys Lys
            100                 105                 110

Arg Asp Leu Lys Cys Cys Met Gly Met Cys Gly Lys Ser Cys Val Ser
        115                 120                 125

Pro Val Lys Ala Ala Val Glu Gly Gly Cys Ser His Leu Gly Gln Ser
    130                 135                 140

Tyr Ala Asp Arg Asp Val Trp Lys Pro Glu Pro Cys Gln Ile Cys Val
145                 150                 155                 160

Cys Asp Ser Gly Ser Val Leu Cys Asp Asp Ile Ile Cys Asp Asp Gln
                165                 170                 175

Glu Leu Asp Cys Pro Asn Pro Glu Ile Pro Phe Gly Glu Cys Cys Ala
            180                 185                 190

Val Cys Pro Gln Pro Pro Thr Ala Pro Thr Arg Pro Pro Asn Gly Gln
        195                 200                 205
```

```
Gly Pro Gln Gly Pro Lys Gly Asp Pro Gly Pro Gly Ile Pro Gly
    210                 215                 220
Arg Asn Gly Asp Pro Gly Ile Pro Gly Gln Pro Gly Ser Pro Gly Ser
225                 230                 235                 240
Pro Gly Pro Pro Gly Ile Cys Glu Ser Cys Pro Thr Gly Pro Gln Asn
                245                 250                 255
Tyr Ser Pro Gln Tyr Asp Ser Tyr Asp Val Lys Ser Gly Val Ala Val
            260                 265                 270
Gly Gly Leu Ala Gly Tyr Pro Gly Pro Ala Gly Pro Pro Gly Pro Pro
        275                 280                 285
Gly Pro Pro Gly Thr Ser Gly His Pro Gly Ser Pro Gly Ser Pro Gly
    290                 295                 300
Tyr Gln Gly Pro Pro Gly Glu Pro Gly Gln Ala Gly Pro Ser Gly Pro
305                 310                 315                 320
Pro Gly Pro Pro Gly Ala Ile Gly Pro Ser Gly Pro Ala Gly Lys Asp
                325                 330                 335
Gly Glu Ser Gly Arg Pro Gly Arg Pro Gly Glu Arg Gly Leu Pro Gly
            340                 345                 350
Pro Pro Gly Ile Lys Gly Pro Ala Gly Ile Pro Gly Phe Pro Gly Met
        355                 360                 365
Lys Gly His Arg Gly Phe Asp Gly Arg Asn Gly Glu Lys Gly Glu Thr
    370                 375                 380
Gly Ala Pro Gly Leu Lys Gly Glu Asn Gly Leu Pro Gly Glu Asn Gly
385                 390                 395                 400
Ala Pro Gly Pro Met Gly Pro Arg Gly Ala Pro Gly Glu Arg Gly Arg
                405                 410                 415
Pro Gly Leu Pro Gly Ala Ala Gly Ala Arg Gly Asn Asp Gly Ala Arg
            420                 425                 430
Gly Ser Asp Gly Gln Pro Gly Pro Pro Gly Pro Pro Gly Thr Ala Gly
        435                 440                 445
Phe Pro Gly Ser Pro Gly Ala Lys Gly Glu Val Gly Pro Ala Gly Ser
    450                 455                 460
Pro Gly Ser Asn Gly Ala Pro Gly Gln Arg Gly Glu Pro Gly Pro Gln
465                 470                 475                 480
Gly His Ala Gly Ala Gln Gly Pro Pro Gly Pro Pro Gly Ile Asn Gly
                485                 490                 495
Ser Pro Gly Gly Lys Gly Glu Met Gly Pro Ala Gly Ile Pro Gly Ala
            500                 505                 510
Pro Gly Leu Met Gly Ala Arg Gly Pro Pro Gly Pro Ala Gly Ala Asn
        515                 520                 525
Gly Ala Pro Gly Leu Arg Gly Gly Ala Gly Glu Pro Gly Lys Asn Gly
    530                 535                 540
Ala Lys Gly Glu Pro Gly Pro Arg Gly Glu Arg Gly Glu Ala Gly Ile
545                 550                 555                 560
Pro Gly Val Pro Gly Ala Lys Gly Glu Asp Gly Lys Asp Gly Ser Pro
                565                 570                 575
Gly Glu Pro Gly Ala Asn Gly Leu Pro Gly Ala Ala Gly Glu Arg Gly
            580                 585                 590
Ala Pro Gly Phe Arg Gly Pro Ala Gly Pro Asn Gly Ile Pro Gly Glu
        595                 600                 605
Lys Gly Pro Ala Gly Glu Arg Gly Ala Pro Gly Pro Ala Gly Pro Arg
    610                 615                 620
```

```
Gly Ala Ala Gly Glu Pro Gly Arg Asp Gly Val Pro Gly Gly Pro Gly
625                 630                 635                 640

Met Arg Gly Met Pro Gly Ser Pro Gly Gly Pro Gly Ser Asp Gly Lys
            645                 650                 655

Pro Gly Pro Pro Gly Ser Gln Gly Glu Ser Gly Arg Pro Gly Pro Pro
        660                 665                 670

Gly Pro Ser Gly Pro Arg Gly Gln Pro Gly Val Met Gly Phe Pro Gly
        675                 680                 685

Pro Lys Gly Asn Asp Gly Ala Pro Gly Lys Asn Gly Glu Arg Gly Gly
    690                 695                 700

Pro Gly Gly Pro Gly Pro Gln Gly Pro Pro Gly Lys Asn Gly Glu Thr
705                 710                 715                 720

Gly Pro Gln Gly Pro Pro Gly Pro Thr Gly Pro Gly Asp Lys Gly
                725                 730                 735

Asp Thr Gly Pro Pro Gly Pro Gln Gly Leu Gln Gly Leu Pro Gly Thr
                740                 745                 750

Gly Gly Pro Pro Gly Glu Asn Gly Lys Pro Gly Glu Pro Gly Pro Lys
        755                 760                 765

Gly Asp Ala Gly Ala Pro Gly Ala Pro Gly Gly Lys Gly Asp Ala Gly
    770                 775                 780

Ala Pro Gly Glu Arg Gly Pro Pro Gly Leu Ala Gly Ala Pro Gly Leu
785                 790                 795                 800

Arg Gly Gly Ala Gly Pro Pro Gly Pro Glu Gly Gly Lys Gly Ala Ala
                805                 810                 815

Gly Pro Pro Gly Pro Pro Gly Ala Ala Gly Thr Pro Gly Leu Gln Gly
                820                 825                 830

Met Pro Gly Glu Arg Gly Gly Leu Gly Ser Pro Gly Pro Lys Gly Asp
            835                 840                 845

Lys Gly Glu Pro Gly Gly Pro Gly Ala Asp Gly Val Pro Gly Lys Asp
850                 855                 860

Gly Pro Arg Gly Pro Thr Gly Pro Ile Gly Pro Pro Gly Pro Ala Gly
865                 870                 875                 880

Gln Pro Gly Asp Lys Gly Glu Gly Gly Ala Pro Gly Leu Pro Gly Ile
                885                 890                 895

Ala Gly Pro Arg Gly Ser Pro Gly Glu Arg Gly Glu Thr Gly Pro Pro
            900                 905                 910

Gly Pro Ala Gly Phe Pro Gly Ala Pro Gly Gln Asn Gly Glu Pro Gly
        915                 920                 925

Gly Lys Gly Glu Arg Gly Ala Pro Gly Glu Lys Gly Glu Gly Gly Pro
    930                 935                 940

Pro Gly Val Ala Gly Pro Pro Gly Gly Ser Gly Pro Ala Gly Pro Pro
945                 950                 955                 960

Gly Pro Gln Gly Val Lys Gly Glu Arg Gly Ser Pro Gly Gly Pro Gly
            965                 970                 975

Ala Ala Gly Phe Pro Gly Ala Arg Gly Leu Pro Gly Pro Pro Gly Ser
            980                 985                 990

Asn Gly Asn Pro Gly Pro Pro Gly Pro Ser Gly Ser Pro Gly Lys Asp
            995                 1000                1005

Gly Pro Pro Gly Pro Ala Gly Asn Thr Gly Ala Pro Gly Ser Pro
    1010                1015                1020

Gly Val Ser Gly Pro Lys Gly Asp Ala Gly Gln Pro Gly Glu Lys
    1025                1030                1035

Gly Ser Pro Gly Ala Gln Gly Pro Pro Gly Ala Pro Gly Pro Leu
```

```
                    1040                 1045                 1050
Gly Ile Ala Gly Ile Thr Gly Ala Arg Gly Leu Ala Gly Pro Pro
    1055                 1060                 1065
Gly Met Pro Gly Pro Arg Gly Ser Pro Gly Pro Gln Gly Val Lys
    1070                 1075                 1080
Gly Glu Ser Gly Lys Pro Gly Ala Asn Gly Leu Ser Gly Glu Arg
    1085                 1090                 1095
Gly Pro Pro Gly Pro Gln Gly Leu Pro Gly Leu Ala Gly Thr Ala
    1100                 1105                 1110
Gly Glu Pro Gly Arg Asp Gly Asn Pro Gly Ser Asp Gly Leu Pro
    1115                 1120                 1125
Gly Arg Asp Gly Ser Pro Gly Lys Gly Asp Arg Gly Glu Asn
    1130                 1135                 1140
Gly Ser Pro Gly Ala Pro Gly Ala Pro Gly His Pro Gly Pro Pro
    1145                 1150                 1155
Gly Pro Val Gly Pro Ala Gly Lys Ser Gly Asp Arg Gly Glu Ser
    1160                 1165                 1170
Gly Pro Ala Gly Pro Ala Gly Ala Pro Gly Pro Ala Gly Ser Arg
    1175                 1180                 1185
Gly Ala Pro Gly Pro Gln Gly Pro Arg Gly Asp Lys Gly Glu Thr
    1190                 1195                 1200
Gly Glu Arg Gly Ala Ala Gly Ile Lys Gly His Arg Gly Phe Pro
    1205                 1210                 1215
Gly Asn Pro Gly Ala Pro Gly Ser Pro Gly Pro Ala Gly Gln Gln
    1220                 1225                 1230
Gly Ala Ile Gly Ser Pro Gly Pro Ala Gly Pro Arg Gly Pro Val
    1235                 1240                 1245
Gly Pro Ser Gly Pro Pro Gly Lys Asp Gly Thr Ser Gly His Pro
    1250                 1255                 1260
Gly Pro Ile Gly Pro Pro Gly Pro Arg Gly Asn Arg Gly Glu Arg
    1265                 1270                 1275
Gly Ser Glu Gly Ser Pro Gly His Pro Gly Gln Pro Gly Pro Pro
    1280                 1285                 1290
Gly Pro Pro Gly Ala Pro Gly Pro Cys Cys Gly Gly Val Gly Ala
    1295                 1300                 1305
Ala Ala Ile Ala Gly Ile Gly Gly Glu Lys Ala Gly Gly Phe Ala
    1310                 1315                 1320
Pro Tyr Tyr Gly Asp Glu Pro Met Asp Phe Lys Ile Asn Thr Asp
    1325                 1330                 1335
Glu Ile Met Thr Ser Leu Lys Ser Val Asn Gly Gln Ile Glu Ser
    1340                 1345                 1350
Leu Ile Ser Pro Asp Gly Ser Arg Lys Asn Pro Ala Arg Asn Cys
    1355                 1360                 1365
Arg Asp Leu Lys Phe Cys His Pro Glu Leu Lys Ser Gly Glu Tyr
    1370                 1375                 1380
Trp Val Asp Pro Asn Gln Gly Cys Lys Leu Asp Ala Ile Lys Val
    1385                 1390                 1395
Phe Cys Asn Met Glu Thr Gly Glu Thr Cys Ile Ser Ala Asn Pro
    1400                 1405                 1410
Leu Asn Val Pro Arg Lys His Trp Trp Thr Asp Ser Ser Ala Glu
    1415                 1420                 1425
Lys Lys His Val Trp Phe Gly Glu Ser Met Asp Gly Gly Phe Gln
    1430                 1435                 1440
```

```
Phe Ser Tyr Gly Asn Pro Glu Leu Pro Glu Asp Val Leu Asp Val
    1445            1450                1455

Gln Leu Ala Phe Leu Arg Leu Leu Ser Ser Arg Ala Ser Gln Asn
    1460            1465                1470

Ile Thr Tyr His Cys Lys Asn Ser Ile Ala Tyr Met Asp Gln Ala
    1475            1480                1485

Ser Gly Asn Val Lys Lys Ala Leu Lys Leu Met Gly Ser Asn Glu
    1490            1495                1500

Gly Glu Phe Lys Ala Glu Gly Asn Ser Lys Phe Thr Tyr Thr Val
    1505            1510                1515

Leu Glu Asp Gly Cys Thr Lys His Thr Gly Glu Trp Ser Lys Thr
    1520            1525                1530

Val Phe Glu Tyr Arg Thr Arg Lys Ala Val Arg Leu Pro Ile Val
    1535            1540                1545

Asp Ile Ala Pro Tyr Asp Ile Gly Gly Pro Asp Gln Glu Phe Gly
    1550            1555                1560

Val Asp Val Gly Pro Val Cys Phe Leu
    1565            1570

<210> SEQ ID NO 28
<211> LENGTH: 11
<212> TYPE: PRT
<213> ORGANISM: Unknown
<220> FEATURE:
<223> OTHER INFORMATION: Sequence typically found in small leucine-rich
      proteoglycans.
<220> FEATURE:
<221> NAME/KEY: MISC_FEATURE
<222> LOCATION: (2)..(3)
<223> OTHER INFORMATION: X at polition 2 or 3 may be any amino acid.
<220> FEATURE:
<221> NAME/KEY: MISC_FEATURE
<222> LOCATION: (5)..(5)
<223> OTHER INFORMATION: X at polition 5 may be any amino acid.
<220> FEATURE:
<221> NAME/KEY: MISC_FEATURE
<222> LOCATION: (7)..(8)
<223> OTHER INFORMATION: X at polition 7 or 8 may be any amino acid.
<220> FEATURE:
<221> NAME/KEY: MISC_FEATURE
<222> LOCATION: (10)..(10)
<223> OTHER INFORMATION: X at polition 10 may be any amino acid.
<220> FEATURE:
<221> NAME/KEY: MISC_FEATURE
<222> LOCATION: (11)..(11)
<223> OTHER INFORMATION: X at polition 11 is selected from L and I only.

<400> SEQUENCE: 28

Leu Xaa Xaa Leu Xaa Leu Xaa Xaa Asn Xaa Xaa
1               5                   10
```

MODIFIED PEPTIDES AND THEIR USES

This application is a divisional of U.S. application Ser. No. 10/554,068, filed Oct. 21, 2005, now U.S. Pat. No. 7,351,522, which is the U.S. national phase under 35 U.S.C. §3138 of PCT International Application No. PCT/GB2004/001719, which has an international filing date of Apr. 21, 2004, designating the United States of America, and claims benefit of British Patent Application No. 0309064.4, which was filed Apr. 22, 2003. The disclosures of each of these prior applications are hereby incorporated by reference herein.

The present invention relates to modified extracellular matrix molecules, to polymers, matrices and gels made therefrom and to their uses in such applications as wound healing.

There is a need for new clinical therapies to treat chronic wounds. The wound care market is vast and the cost to health authorities treating foot and leg ulcers is an estimated $7,000 million p.a. worldwide (FDA website www.fda.gov/). The existing treatments for such wounds include glutaraldehyde—cross-linked collagen implants, type I collagen gels containing cultured fibroblasts or fibroblasts supported on polyacid substrates. The use of chemical substrates, exogenous cells and crosslinking compounds increases the risk of implant rejection, antigenic responses and poor integration at the wound margin. Also, dressings containing pre-cultured cells are difficult to scale up and deliver fresh to the patient.

Furthermore, the standard treatment for chronic wounds, such as venous ulcers, is the use of absorbent or non-absorbent dressings in conjunction with compression therapy. However, this approach is only moderately effective, is uncomfortable for the patient, can take several months to take effect and recurrence occurs in the majority of cases where treatment is completed. Therefore, there is a an urgent need for the treatment and management of chronic wounds that avoids repeated applications of expensive dressings and which fail to address the underlying cellular and molecular mechanisms contributing to the pathogenesis of delayed healing. One of the most important contributing factors that results in the standard treatments for wound healing being only moderately effective is the markedly reduced deposition of collagen at the wound site associated with impaired cellular infiltration.

Most cells, whether simple unicellular organisms or cells from human tissue, are surrounded by an intricate network of macromolecules which is known as the extracellular matrix (ECM) and which is comprised of a variety of proteins and polysaccharides. A major protein component of the ECM is a family of related proteins called the collagens which are thought to constitute approximately 25% of total proteins in mammals. There are at least 26 genetically distinct types of collagen molecule, some of which are known as fibrillar collagens (collagen types I, II, III, V and XI) because they typically form large fibres, known as collagen fibrils, that may be many micrometers long and may be visualized by electron microscopy.

Collagen fibrils are comprised of polymers of collagen molecules and are produced by a process involving conversion of procollagen to collagen molecules that then assemble to form the polymer. Procollagen consists of a triple stranded helical domain in the centre of the molecule and has non-helical domains at the amino terminal (known as the N-terminal propeptide) and at the carboxyl terminal (known as the C-terminal propeptide). The triple stranded helical domain is made up of three polypeptides which are known as α chains. Procollagen is made intracellularly from pro-α chains (α chains with N and C-terminal forming propeptide domains). Pro-α chains are synthesized on membrane-bound ribosomes following which the pro-α chains are inserted into the endoplasmic reticulum. Within the endoplasmic reticulum the pro-α chains are assembled into a procollagen molecule. Procollagen is secreted into the extracellular environment where it is then converted into collagen by the action of procollagen N-proteinases (which cleave the N-terminal propeptide) and procollagen C-proteinases (which cleave the C-terminal propeptide). Once the propeptides have been removed the collagen molecules thus formed are able to self-assemble spontaneously to form the collagen fibrils. The rate determining step in the formation of collagen fibrils is the removal of the C-propeptides by procollagen C-proteinases.

Collagen fibrils interact with other fibrils and also other components of the extracellular matrix to form connective tissues in vivo. Fibrils will assemble in vitro and will interact to form a collagen matrix or gel. Such collagen matrices have various industrial uses. For instance, collagen-based biomedical products are used in the cosmetic and aesthetic enhancement markets as implants and for smoothing lines, wrinkles and facial scars. Collagen based products are also used in the production of artificial skins (e.g. for treating burns patients), wound dressings and the like.

Whilst collagen based products have been extensively adopted, their performance is far from satisfactory and a number of contra-indications and adverse reactions are known. Some of the problems are related to the fact that many of these products are based on animal collagen (e.g. from bovine hide) and as such can give rise to allergic and inflammatory reactions and infections. Other collagen products are derived from cadaver tissue and it is suggested that they result in reduced inflammation and allergic reactions. However such products are expensive to manufacture and difficulties in controlling product quality can lead to variation in performance.

Another important function of the ECM is the storage and presentation of growth factors to cells. Proteoglycan components of the ECM play a central role in the regulation of the activity of a number of growth factors and therefore represent powerful pathophysiological modulators.

A well known example of a family of proteoglycans has a core protein of about 107 kDa that consists mainly of leucine-rich repeats of 20-24 amino acids. These proteins are known as Small Leucine-Rich Proteoglycans (SLRPs) and typically contain the sequence $LX_2LXLX_2NX(L/I)$ (Seq ID NO. 29) where L=leucine; N=asparagines; I isoleucine are in the specified conserved positions and X=any amino acid.

The SLRP family comprises at least 4 members, namely decorin, biglycan, fibromodulin and lumican (all of which were characterised in some detail in the late 1980s/early 1990s). These proteoglycans have specialized functions in cell cycle regulation, in tissue repair and in modulating the mechanical properties of tissues by their interaction with collagen fibrils. Decorin and related proteoglycans have also been reported to bind to and modulate the activity of various growth factors including members of the transforming growth factor β (TGF-β) family. Growth factors such as the TGF-βs have a major influence on cell activity and ECM remodelling. There are at least 5 different TGF-βs (TGF-β1-TGF-β5) and their chemical structures and activity have been widely reported (e.g. see Sporn et al. J. Cell Biol. 105: 1039 (1987).

A major pathophysiological activity of TGF-βs (particularly TGF-β1 and TGF-β2) is the promotion of wound healing. However this is often associated with increased scar formation and fibrosis. In fact, clinical interest in the modulation of TGF-β has been associated with inhibiting its activity in order to reduce scar formation (although this may compromise the rate of wound healing). For instance, WO 92/17206 discloses compositions which inhibit the activity of TGF-β1 and TGF-β2 and are particularly beneficial for reducing scar formation.

Another proteoglycan that is known to bind to TGF-βs is the type III TGF-β receptor. This proteoglycan is a cell membrane receptor that can act as a reservoir for TGF-β and is also known as betaglycan (or soluble betaglycan if cleaved from the cell membrane and found free in the ECM).

The modulation of the activity of growth factors such as TGF-β is of significant clinical interest. Various parties have investigated the usefulness of proteoglycans as pharmacologically active agents. For instance, the use of such molecules to regulate fibrotic conditions, wound healing and scarring is contemplated (1) WO 93/09800—relating to the use of decorin and related proteoglycans as agents for preventing or reducing scarring; and (2) WO 97/05892—which discloses the use of soluble betaglycan as an anti-scarring agent The Applicant's co-pending application No. PCT/GB2002/004785 relates to novel modified procollagen molecules wherein at least one N-terminal domain of the molecule contains a polypeptide sequence from at least part of a proteoglycan protein core. The production of collagen gels and matrices from such modified procollagens has been found to assist in wound healing by attracting growth factors to the wound site. Furthermore, the procollagen matrices have been found to have increased resistance to cell shrinkage.

Despite these advances there remains a need to develop further medicaments for assisting in wound healing whilst avoiding or reducing the drawbacks experienced with the prior art applications.

Laminins are a large family of multifunctional glycoproteins which are distributed ubiquitously within basement membranes. The laminins have key roles in development, differentiation and migration due to their ability to interact with cells by means of their high affinity binding sites via cell-surface reactors including integrins and type IV collagen. They are composed of three genetically distinct chains, being αβγ heterotrimeric proteins that assemble into a cruciform molecule with one long arm and three short arms. There are 18 different laminin isoforms, including Laminin-1, Laminin-2, Laminin-5 and Laminin-10.

The laminins are known to bind keratinocytes and provide survival and differentiation signals to epithelial cells and keratinocytes which are critical cells needed for re-epithelialization of dermal wounds.

A further molecule that is secreted into the extracellular matrix and is involved in wound healing is secretory leukocyte protease inhibitor (SLPI). This molecule, also known as antileukoprotease, is an 11.7 kD cationic inhibitor of neutrophil elastase. In addition to protecting against injury, it has also been shown that it functions as an antimicrobial and anti inflammatory. SLPI is produced naturally by the blood and modifies levels of elastase, a substance which breaks down the skin.

It is an object of the present invention to address problems associated with prior art medicaments and delivery systems. A further object of the present invention is to address problems associated with collagen matrices and gels known in the art.

The present invention is based upon the realization by the inventors that desirable functional characteristics may be introduced into a composition such as a medicament or collagen matrix by designing modified pro-α chains according to a first aspect of the present invention which may be trimerized to form procollagen derivatives. These in turn may be converted to collagen monomers (with retained propeptides) and subsequently polymerized. This allows the synthesis and assembly of novel collagen polymers having new biological properties.

To this end, a first aspect of the present invention provides a modified pro-α chain comprising a triple helical forming domain linked to at least an N-terminal domain characterised in that the N-terminal domain contains a polypeptide sequence from at least part of a laminin glycoprotein or at least part of a secretory leukocyte protease inhibitor or functional derivatives thereof.

The inventors have found that they can employ molecular biology techniques to modify the gene encoding pro-α chains such that modified pro-α chains according to the first aspect of the invention may be expressed therefrom. Therefore according to a second aspect of the invention there is provided a DNA molecule encoding modified pro-α chains according to the first aspect of the invention.

The inventors then trimerized modified pro-α chains according to the first aspect of the invention to form a procollagen molecule with a modified N propeptide. The trimer may be a homotrimer of modified pro-α chains or may be a heterotrimer also containing natural pro-α chains. Therefore according to a third aspect of the present invention there is provided a procollagen molecule comprising a trimer of pro-α chains characterised in that at least one of the pro-α chains is a pro-α chain according to the first aspect of the invention.

The inventors then performed further experiments that established that procollagen molecules according to the third aspect of the invention may be polymerized to form a collagen polymer. Furthermore they have established that they can regulate N-propeptide cleavage by modifying the N-terminal domain such that the domain's susceptibility to cleavage is altered such that the collagen polymer retains N-propeptides or derivatives thereof upon its surface. This may be achieved by designing procollagen molecules according to the third aspect of the invention such that they are resistant to procollagen N-proteinases. Alternatively, the molecules may only be partially cleaved or cleaved more slowly. It is preferred that pro-α chains according to the first aspect of the invention are also modified such that they contain an amino acid sequence that confers resistance to procollagen N-proteinases.

Alternatively the inventors have found that they can assemble collagen polymers with retained N-propeptides in an environment in which procollagen N-proteinase is either inhibited or absent.

According to a fourth aspect of the invention there is provided a collagen polymer with at least some of the collagen monomers contained therein having retained N-terminal ends characterised in that at least some of the retained N-terminal ends contain a polypeptide sequence encoding at least part of a laminin glycoprotein, at least part of a secretory leukocyte protease inhibitor or functional derivatives thereof.

Collagen polymers according to the fourth aspect of the invention may form collagen fibrils.

Additionally, the C-terminal domains of the procollagens making up the collagen polymer may be removed, for example using a procollagen C-proteinase, such as bone morphogenetic protein (BMP-1). This has been found to result in the N-terminal propeptides being presented at the fibril surface.

EP-A-0 985 732 contemplates the production of chimeric collagens with biologically active peptides (e.g. a growth factor per se) fused to the N-terminal and which can polymerize to form fibrils. However EP-A-0 985 732 does not contemplate or suggest the addition of the polypeptide sequence of at least part of a laminin or secretory leukocyte protease inhibitor (SLPI) to the N terminal domain of a pro-α chain according to the first aspect of the invention.

Modified pro-α chains according to the first aspect of the invention are preferably modified forms of fibrillar forming procollagens (e.g. modified forms of type I, II, III, V or XI pro-α chains). Preferably the molecule is a modified type III pro-α chain. This type is preferred because it can co-assemble with type I collagen and can also form a homotrimer. It is most preferably a modified proα1(III) chain.

It is preferred that only part of a laminin molecule is attached to the pro-α chain. More preferably, the N-terminal ends are derived from the globular domains of an α-chain of a laminin molecule. It is most preferred that the N-terminal end comprises the amino acid sequence for at least the G3 globular domain of the α-chain. Alternatively, the N-terminal may comprise the amino acid sequence for the G1 to G3 domains.

In a preferred embodiment of the invention, the N-terminal sequence of the pro-α chain is replaced with at least part of the amino acid sequence of the α3-chain of Laminin-5 since Laminin-5 has a high affinity for cells of epithelial origin.

In the case of the replacement of the N-terminal end with the polypeptide sequence encoding at least part of a secretory leukocyte protease inhibitor, it is preferred that the entire sequence of the inhibitor is attached to the N-terminal domain.

Preferably, the N-propeptide sequence of the pro-α chain replaces the procollagen N-propeptide sequence prior to N100 to ensure that the collagen retains its signal sequence.

Natural N-terminal propeptide forming domains may be modified such that essentially all of the N-terminal end is replaced by a laminin glycoprotein or SLPI. The extent to which the normal N-terminal propeptide forming domain is replaced is less critical than ensuring that keratinocyte-binding functionality of the laminin molecule or the elastase inhibitory functionality of the SLPI molecule is introduced. Accordingly the N-terminal propeptide forming domain may be totally replaced, partially replaced or even maintained in its entirety (provided it has the required functionality added).

It is desirable to make some modified pro-α chains according to the present invention that trimerize to form procollagens that are resistant to N propeptide cleavage. Therefore some preferred molecules according to the first aspect of the invention have amino acid sequences defining a modified N-proteinase cleavage site which renders procollagens resistant to such cleavage. People with the Ehlers Danlos syndrome type VII have mutations in a collagen gene which abolishes the N-proteinase cleavage site on the procollagen molecule. Therefore with knowledge of this mutation the region of the domain requiring such modification is easily identified.

The region between the helical forming domain and N-propeptide forming domain of the pro-α chain (the so called hinge domain) is most suitably modified to confer resistance to N-proteinases. For instance, Pro-Gln at the cleavage site may be altered to Leu-Pro.

Modified pro-α chains according to the first aspect of the invention may be formed by direct chemical synthesis or by in vitro amino acid polymerization followed by protein folding and, if appropriate, glycosylation of the modified polypeptide sequence. However it is preferred that molecular biology techniques are used to design a DNA molecule according to the second aspect of the invention and express the modified pro-α chain in a cell or expression system containing such a DNA molecule.

The DNA molecule according to the second aspect of the invention may be formed by manipulating the bases encoding the N-terminal propeptide forming domains such that amino acids are added, substituted or deleted. It is preferred that a nucleotide sequence encoding a laminin, SLPI or functional derivatives thereof is inserted into the bases encoding the N propeptide forming domain. It is particularly preferred that a nucleotide sequence encoding at least the G3 domain of the α-chain of a laminin glycoprotein or all of the SLPI molecule is inserted into the bases encoding the N propeptide forming domain.

Preferred modifications include the insertion of a nucleotide sequence encoding the G3 or the G1, G2 and G3 domains of the α-3 chain of Laminin-5.

Alternatively the bases encoding an N propeptide forming domain of a natural pro-α chain may be completely excised and replaced with bases encoding at least one of the globular domains of an α-chain of laminin or those encoding the SLPI molecule.

According to a preferred embodiment of the invention, the DNA molecule may encode a C-propeptide domain and an α-chain of a pro-α chain and may have the "natural" N-propeptide entirely replaced by a sequence encoding at least one globular domain of an α-chain of a laminin glycoprotein or the SLPI protein.

As previously indicated it is desirable to make some pro-α chains, procollagens or collagen polymers according to the present invention resistant to N propeptide cleavage. Therefore some preferred DNA molecules according to the second aspect of the invention have DNA sequences encoding a modified N-proteinase cleavage site which alters the proteins expressed therefrom resistance to such cleavage. Preferably, the expressed proteins are resistant to cleavage. Alternatively, cleavage in the expressed protein may be partial or slower than in the un-modified protein. It is preferred that the region between the helical forming domain and N-propeptide forming domain of the pro-α chain (the so called hinge domain) is mutated to confer resistance to N-proteinases. For instance, nucleotides encoding Pro-Gln at the cleavage site may be altered to nucleotides encoding Leu-Pro.

The DNA molecule may be incorporated within a suitable vector to form a recombinant vector. The vector may for example be a plasmid, cosmid or phage. Such vectors will frequently include one or more selectable markers to enable selection of cells transfected with the said vector and, preferably, to enable selection of cells harbouring the recombinant vectors that incorporate the DNA molecule according to the second aspect of the invention.

Standard molecular biology techniques may be used to construct vectors comprising DNA molecules according to the second aspect of the invention. Preferred constructs and expression systems are described in more detail in the Examples.

Vectors may be expression vectors and have regulatory sequences to drive expression of the DNA molecule. Vectors not including such regulatory sequences may also be used and are useful as cloning vectors for the purposes of replicating the DNA molecule. When such vectors are used the DNA molecule will ultimately be required to be transferred to a suitable expression vector which may be used for production of the procollagen derivative of the invention.

Replication of the DNA molecule in cloning vectors or expression of the protein product from recombinant expression vectors is performed within a suitable host cell. The DNA molecule may be incorporated within a vector within the host cell. Such host cells may be prokaryotic or eukaryotic. Eukaryotic hosts may include yeasts, insect and mammalian cells. Hosts used for expression of the protein encoded by the DNA molecule are ideally stably transformed, although the use of unstably transformed (transient) hosts is not precluded.

A preferred host cell is the HEK293 cell line and derivatives thereof.

The DNA molecule of the invention may also be incorporated in a transgene construct designed for expression in a transgenic plant or, preferably, animal. Transgenic animals which may be suitably formed for expression of such transgene constructs, include birds such as domestic fowl, amphibian species and fish species. The protein may be harvested from body fluids or other body products (such as eggs, where appropriate). Preferred transgenic animals are (non-human) mammals, particularly placental mammals. An expression product of the DNA molecule of the second aspect of the invention may be expressed in the mammary gland of such mammals and the expression product may subsequently be recovered from the milk. Ungulates, particularly economically important ungulates such as cattle, sheep, goats, water buffalo, camels and pigs are most suitable placental mammals for use as transgenic animals according to the invention. The generation and usefulness of such mammalian transgenic mammary expression systems is both generally, and in certain instances specifically, disclosed in WO-A-8800239 and WO-9005188.

It is preferred that the host contains suitable intracellular facilities for the assembly of the procollagen derivative of the first aspect of the invention from the protein products of the DNA molecule of the second aspect of the invention. In particular, expression hosts, particularly transgenic animals, may contain other exogenous DNA the expression of which facilitates the expression, assembly, secretion or other aspects of the biosynthesis of procollagen derivatives of the third aspect of the invention and even collagen polymers according to the fourth aspect of the invention. For example, expression hosts may co-express prolyl 4-hydroxylase, which is a post translation enzyme important in the natural biosynthesis of procollagens, as disclosed in WO-9307889.

DNA, particularly cDNA, encoding natural pro-α chains is known and available in the art. For example, WO-A-9307889, WO-A-9416570 and the references cited in both of them give details. Such DNA may be used as a convenient starting point for making a DNA molecule of the present invention. Recombinant techniques may be used to derive the DNA molecule of the invention from such a starting point.

DNA sequences, cDNAs, full genomic sequences and minigenes (genomic sequences containing some, but not all, of the introns present in the full length gene) may be inserted by recombinant means into a DNA sequence coding for naturally occurring pro-α chains (such as the starting point DNA mentioned above) to form the DNA molecule according to the second aspect of the invention. Because of the large number of introns present in collagen genes in general, experimental practicalities will usually favour the use of cDNAs or, in some circumstances, minigenes. The inserted DNA sequences, cDNAs, full genomic sequences or minigenes code for amino acids which when expressed and assembled into a procollagen according to the third aspect of the invention give rise to a desired modification in the N-terminal domain of such a procollagen derivative.

Any of the DNA material used in these methods (including the DNA sequences, cDNAs, full genomic sequences and minigenes; the DNA molecule according to the second aspect of the invention and vectors) may be prepared by any convenient method involving coupling together successive nucleotides, and/or ligating oligo- and/or poly-nucleotides, including in vitro processes. However recombinant DNA technology forms the method of choice.

A preferred vector for DNA molecules according to the second aspect of the invention is the episomally replicating plasmid pCep4. This plasmid allows high levels of expression of cloned DNA molecules in cell-lines such as HEK293 transfected with the EBV nuclear antigen.

Collagen polymers in accordance with the fourth aspect of the invention may be of a number of forms. Cylindrical polymers similar to collagen fibrils are generated from mixtures of collagen molecules and collagens derived from procollagens according to the third aspect of the invention when collagen molecules are the major component. Alternatively, sheet-like structures may be formed by using procollagen derivatives according to the third aspect of the invention in the absence of, or substantially in the absence of, normal collagen molecules.

A remarkable feature of collagen polymers according to the fourth aspect of the invention is that the modified N-terminal propeptides are located to the surface of the polymer/fibril so formed, particularly in the case where the C-terminal domain of the procollagen has been removed. The inventors have demonstrated that fibrils formed from mixtures of natural collagens and modified procollagens according to the third aspect of the invention exhibit the modified N-propeptides at the fibril surface whereas the natural collagens (i.e. those without retained N-propeptides) form the core of the fibril. The arrangement of the molecules in the fibril optimizes presentation of the N-propeptides to the interfibrillar space.

Additionally, the inventors were able to form collagen matrices from procollagen molecules according to the third aspect of the invention and/or collagen polymers according to the fourth aspect of the invention. Said collagen matrices form an important fifth aspect of the invention.

Preferably, the matrix is characterised by the fact that at least some of the collagen monomers have a N terminal domain containing at least part of a laminin glycoprotein or at least part of a secretory leukocyte protease inhibitor.

The collagen matrices according to the fifth aspect of the invention have several advantages over known collagen matrices. The incorporation of the globular domain of a laminin glycoprotein into the collagen matrix promotes keratinocyte crawling due to their keratinocyte binding properties and thereby accelerate re-epithelialization. Thus, the matrices may be used to recruit viable cells from wound margins.

Furthermore, the incorporation of SLPI domain into the collagen matrices also aids wound healing, provides antimicrobial and antiinflammatory properties and reduces breakdown of the skin.

Collagen matrices according to the fifth aspect of the invention are preferably made from human recombinant DNA molecules according to the second aspect of the invention. When this is the case, a third advantage is that the matrices are less likely to cause allergic and inflammatory responses when administered to humans.

A collagen matrix may be formed by neutralizing and warming acidic solutions of collagen monomers or procollagens (in the presence of suitable proteinases). Under such conditions the collagen monomers spontaneously self-assemble into polymeric fibrils that then become entangled to form a hydrated and porous gel. The rigidity of such a gel is, at least in part, dependent on the concentration of the collagen used to form the gel and on the diameter of the collagen fibrils formed. The collagen matrix or gel assumes the shape of the container in which it is formed. Therefore, gels can be made that are thin (millimeters) in one dimension and extensive (centimeters or larger) in other dimensions. Such matrices can be suitably shaped to form the basis of replacement skin or cornea. Alternatively, collagen gels can be cast in moulds that have the shape of long bones (cylindrical and long), jaw bones (sickle shaped or curved), articular cartilage (disc shaped), tendon (rope shaped) or ligament (shaped like a strap).

Collagen polymers and matrices according to the fourth and fifth aspects of the invention may comprise exclusively recombinant collagen derived from modified procollagen molecules according to the invention. Alternatively such collagen polymers or matrices may be mixtures of modified collagens or modified procollagens according to the invention and collagen extracted from tissue or cell cultures, such as is available from commercial sources. For example, collagen polymers according to the fourth aspect of the invention may be combined with bovine type I collagen to form a matrix according to a fifth aspect of the invention.

Procollagens or collagens according to the present invention may be used to coat the surfaces of collagen fibrils in a gel or matrix formed from natural collagens (e.g. bovine collagens) or they may be incorporated into the fibrils during gel formation. The new functional moieties introduced into the procollagens or collagens are thereby presented to the surface of the collagen fibrils where they can interact with cells or influence cellular function. The procollagens may be applied as a soluble precursor with a procollagen C-proteinase such as BMP-1 which converts the soluble procollagen to fibril-forming collagen having its N-terminal domain retained to allow gel formation in situ. This enables the modified collagen to integrate and mesh with collagen fibrils at the point of application.

Molecules according to the first-fifth aspects of the invention may be employed in a research setting for exploring a wide range of biological phenomenon from cell adhesion to wound healing and from cell differentiation and apoptosis to the manufacture of wound dressings with improved molecule and cell binding properties. However, a preferred use of the molecules is in the formation of collagen matrices which may be used for medical or cosmetic purposes.

According to a sixth aspect of the present invention there is provided the use of a molecule or matrix according to any one of the first-fifth aspects of the invention for the treatment of medical conditions.

According to a seventh aspect of the present invention there is provided the use of a molecule or matrix according to any one of the first-fifth aspects of the invention for the manufacture of a medicament for use in the treatment of wounds or fibrotic disorders.

According to a eighth aspect of the present invention there is provided a method of treating wounds comprising administering to a subject in need of treatment a therapeutically effective amount of a molecule or matrix according to any one of the first-fifth aspects of the invention.

It is preferred that the medical conditions treated are conditions that are at least partially characterised by remodelling of the ECM.

Whilst the above considerations mainly apply to conditions, disorders or diseases of man it will be appreciated that wound healing can also be problematic in other animals, particularly veterinary or domestic animals (e.g. horses, cattle, dogs, cats etc). For instance abdominal wounds or adhesions are a major reason for having to put down horses (particularly race horses), as are tendon and ligament damage leading to scarring or fibrosis.

Molecules according to the third and fourth aspects of the invention and a matrix according to the fifth aspect of the invention may be formulated into a various types of medicament. The medicament of the invention may take a number of different forms depending, in particular on the manner in which the medicament is to be used. Thus, for example, the medicament may be in the form of a liquid, ointment, cream, gel, hydrogel, powder, aerosol or an implantable device (e.g. by conjugation to a biopolymer sponge).

Molecules according to the third and fourth aspects of the invention may be administered directly (e.g. in liquid form). However, it is preferred that the molecules are incorporated into a wound dressing, an implantable device, artificial skin or tissue etc.

It is preferred that the medicaments are for topical application. The medicament may be most suitably used for topical application to the skin or wound area.

Medicaments comprising modified procollagens, collagens or collagen fibrils may be delivered by means of an aerosol (e.g. for delivery to fibrotic conditions of the lung).

It will be appreciated that the vehicle of the medicament should be one which is well tolerated by the patient and allows release of the collagen polymer to the wound or site of fibrosis. The vehicle will ideally be sterile and may be combined with excipients and/or stabilizers as well as the molecule to form the medicament. Such a vehicle is preferably biodegradeable, bioresolvable, bioresorbable and/or non-inflammatory.

The medicament may be used in a number of ways. Thus, for example, it may be applied in, and/or around a wound of a patient to provide the desired promotion of wound healing. If the composition is to be applied to an "existing" wound, then the pharmaceutically acceptable vehicle will be "mild" enough such that it does not cause an inflammatory response or is toxic to the tissue. Clearly, the inclusion of modified collagen containing the SLPI molecule will assist in reducing any inflammatory response.

Molecules according to the third or fourth aspects of the invention may be provided on a sterile dressing or patch which may be used to cover or even pack a wound or fibrotic site.

The medicament may be provided as an implantable device from which it may be released better. For instance, it may be released by biological dissolution or degradation of the device. Alternatively an external stimulus, such as ultrasound, may cause release of the procollagen, collagen monomer or collagen polymer.

It is also possible to use medicaments in accordance with the invention in a prophylactic manner. For instance, the medicament may be applied prior to surgery so as to provide for regulation of healing of the subsequently formed surgical wound.

A collagen matrix may then be administered to a subject (e.g. to the skin, cartilage, muscle or neural tissues) in the form of a semi-solid gel. Alternatively a more solid matrix may be formed which may be used in the formation of a wound dressing, an implantable device, artificial skin or tissue etc.

Artificial skins comprising matrices according to the fifth aspect of the invention may comprise ECM components alone or may further comprise cultured cells such as fibroblasts and/or endothelial cells. Artificial skins containing such cells are known as "living" replacement skin products.

It is preferred that the collagen matrices are formed into artificial skin for topical application to dermal wounds or burns. The artificial skins comprising matrices according to the fifth aspect of the invention are particularly useful for treating severe wounds, extensive wounds, chronic wounds (e.g. dermal ulcers) and burns.

It will be appreciated that the matrix should be hydrated in a pharmaceutically acceptable vehicle. The vehicle should be sterile and "mild" enough such that it does not cause an inflammatory response or is toxic to the tissue being treated.

The matrix may be incorporated into a sterile dressing or patch which may be used to cover or even pack a wound or fibrotic site.

In a preferred embodiment, the matrix is applied to a dressing, such as a Combiderm N dressing and then dehydrated. The dehydrated gel carried on the dressing is then applied to a wound.

The matrix may be provided as an implantable device from which the matrix per se may be released into the wound site. Release may be caused by biological dissolution or degradation of the device. Alternatively an external stimulus, such as ultrasound, may cause release of the collagen polymer.

A collagen matrix according to the fifth aspect of the invention may be cast into a sheet. Preferred sheets may be 1—several millimeters thick by several centimeters square. Such sheets can be acellular or populated with mesenchymal and/or fibroblastic cells to generate an artificial skin, cartilage, bone or cornea, or endothelial cells to produce cardiovascular patches. The cells may be obtained from a patient or a tissue-matched donor, stem cells from a patient or a donor, or cells that have been amplified in culture. Such matrices may be coated with molecules according to the third and fourth aspects of the invention to confer keratinocyte binding functionality or elastase inhibition to the matrix. The collagen matrix or collagen-cell construct can be stored under aseptic conditions and at physiological temperatures or under cryogenic storage conditions until needed.

It will be appreciated that the amount of molecule required to modulate healing and fibrosis depends on a number of factors such as its biological activity and bioavailability, which in turn depends on the mode of administration and the physicochemical properties of the particular molecule used. For example, the amount of collagen matrix required will depend upon factors such as the concentration of the gel (this may be required to be aqueous, viscous or relatively solid—depending upon the clinical need) and the proportion of collagens with the new functional moieties contained therein. Other factors include:

A) The specific condition to be treated.
B) The severity of the condition.
C) The age of the subject.
D) The site of delivery.
E) The half-life of the molecule in the subject being treated.

The frequency of administration will also be influenced by the above mentioned factors and particularly the half-life of the compound or matrix within the subject being treated.

Generally, a subject being treated will derive benefit from the application of the modified procollagen, collagen monomer or collagen polymer, if it as administered to a wound within 7 days of wounding, preferably within 48 hours of wounding, more preferably within 24 hours of wounding and even more preferably within 12 hours of wounding. The medicament should be administered to a subject suffering from a fibrotic condition according to a clinicians directions. This may be as soon as diagnosis has occurred. Therapy should continue until the wound has healed or fibrotic disorder cleared to a clinicians satisfaction.

When used as a prophylactic (e.g. before surgery) the medicament should be administered as soon as it is recognized that a wound may occur or fibrotic disorder may develop. For instance, a cream or ointment containing collagen polymer according to a fourth aspect of the invention may be applied to a site on the skin of a subject where elective surgery is to be performed and an increased rate of wound healing is subsequently desired. In this case, the medicament may be applied during the preoperative preparation of the subject or it may even be desirable to apply it in the hours or days preceding the surgery (depending upon the health status and age of subject as well as the size of the wound to be formed).

Frequency of administration will depend upon the biological half-life of the molecule used. Typically a cream or ointment should be administered to a target tissue such that the concentration of the molecule at the wound site is maintained at a level suitable for having a therapeutic effect. This may require administration daily or even several times daily.

Known procedures, such as those conventionally employed by the pharmaceutical industry (e.g. in vivo experimentation, clinical trials etc), may be used to establish specific formulations of compositions and precise therapeutic regimes (such as daily doses of the compounds and the frequency of administration).

Generally, for use in accordance with the invention a medicament containing an amount of 1 ng to 10 mg of collagen polymer, more preferably 1 μg to 1 mg of collagen polymer, may be applied per centimeter of linear wound. Purely by way of example, a medicament containing about 10 μg collagen polymer is suitable for application to a 1 cm linear incisonal wound. Higher doses are required to stimulate the healing of chronic wounds compared to acute wounds.

Efficacy of medicaments, and particularly those formulated for application to chronic wounds, have enhanced efficacy when combined with a protease inhibitor (e.g. galadrin) Protease inhibitors prevent or retard the degradation of the collagen by proteases which may be found in high levels in wounds, particularly chronic wounds. The protease inhibitor is preferably a broad spectrum protease inhibitor.

It will be appreciated that the molecules and matrices according to the third, fourth and fifth aspects of the invention may be used in combination with other wound healing or anti-fibrotic agents or followed by another agent (e.g. for prevention of scarring).

It will be appreciated that matrices according to the fifth aspect of the invention (used to treat medical conditions, cosmetically or otherwise) may be formed in situ (i.e. at the tissue/site where the matrix is required). For instance, a solution or slurry of collagen polymers according to the fourth aspect of the invention may be used to soak a wound dressing. Gel formation may be induced when the dressing is used (e.g. a reaction may initiated when the dressing is removed from its package or contacts a wound site). Alternatively a solution of collagen polymers according to the fourth aspect of the invention, or even procollagens according to the third aspect of the invention may be injected into a target body tissue and matrix formation allowed to proceed with native collagens.

DNA molecules according to the second aspect of the invention may be used in gene therapy techniques. Therefore according to a ninth aspect of the present invention there is provided a delivery system for use in a gene therapy technique, said delivery system comprising a DNA molecule according to the second aspect of the invention which is capable of being transcribed to lead to the expression of a modified pro-α chain according to the first aspect of the invention at a wound site or site of fibrosis.

According to a tenth aspect of the present invention there is provided the use of a delivery system as defined in the preceding paragraph for use in the manufacture of a medicament for treating wounds or fibrotic disorders.

According to an eleventh aspect of the present invention there is provided a method of treating a wound or fibrotic condition which consists of administering to a patient in need of treatment a therapeutic dose of a delivery system as defined above.

The delivery systems are highly suitable for achieving sustained levels of a procollagen molecule according to the third aspect of the invention or a collagen polymer according to the fourth aspect of the invention at a wound site or site of fibrosis over a longer period of time than is possible for most conventional delivery systems. Modified pro-α chains may be continuously expressed from cells at the site that have been transformed with the DNA molecule of the second aspect of the invention. Therefore, even if the modified procollagen or collagen polymer has a very short half-life as an agent in vivo, therapeutic doses may be continuously expressed from the treated tissue.

Furthermore, the delivery system of the invention may be used to provide the DNA molecule without the need to use conventional pharmaceutical vehicles such as those required in ointments or creams that are contacted with the wound or site of fibrosis. This is particularly beneficial as it can often be difficult to provide a satisfactory vehicle for a compound for use in wound healing (which are required to be non-inflammatory, biocompatible, bioresorbable and must not degrade or inactivate the active agent (in storage or in use)).

The delivery system is such that the DNA molecule is capable of being expressed (when the delivery system is administered to a patient) to produce modified pro-α chains which form procollagens and then collagen polymers with the modified N terminals. These modified N terminals then interact with cells or biologically active agents at the site of the wound or fibrosis and thereby treat the condition.

The DNA molecule may be contained within a suitable vector to form a recombinant vector. The vector may for example be a plasmid, cosmid or phage. Such recombinant vectors are highly useful in the delivery systems of the invention for transforming cells with the DNA molecule. The vector may be pCEP4 or a similar vector.

Recombinant vectors may also include other functional elements. For instance, recombinant vectors can be designed such that the vector will autonomously replicate in the nucleus of the cell. In this case, elements which induce DNA replication may be required in the recombinant vector. Alternatively the recombinant vector may be designed such that the vector and recombinant DNA molecule integrates into the genome of a cell. In this case DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The DNA molecule may (but not necessarily) be one which becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour instable or transient transformation of differentiated cells in the subject being treated. When this is the case, regulation of expression may be less important because expression of the DNA molecule will stop when the transformed cells die or stop expressing the protein (ideally when the wound, fibrosis or scarring has been treated or prevented).

The delivery system may provide the DNA molecule to the subject without it being incorporated in a vector. For instance, the DNA molecule may be incorporated within a liposome or virus particle. Alternatively the "naked" DNA molecule may be inserted into a subject's cells by a suitable means e.g. direct endocytotic uptake.

The DNA molecule may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of plasmid DNA directly to the wounded area topically or by injection.

Whilst the above considerations mainly apply to wounds of man it will be appreciated that wound healing, can also be problematic in other animals (especially veterinary and domestic animals such as cattle, horses, dogs, cats etc). For instance, abdominal wounds or adhesions are a major reason for having to put down horses. The medicaments and delivery systems discussed above are also suitable for use in the healing of such animals.

The present invention will now be further described with reference to the following non-limiting examples and figures in which:

FIG. 1 schematically illustrates a natural procollagen molecule;

FIG. 2 schematically illustrates lam-procollagen, a procollagen molecule according to the third aspect of the invention;

FIG. 3 illustrates the nucleotide sequence of a DNA molecule according to the second aspect of the invention from Example 1;

FIG. 4 illustrates the amino acid sequence of a modified pro-α chain according to the first aspect of the invention from Example 1;

FIG. 6 illustrates the nucleotide sequence of a DNA molecule according to the second aspect of the present invention from Example 2;

FIG. 7 illustrates the amino acid sequence of a modified pro-α chain according to a first aspect of the invention from Example 2;

FIG. 8 illustrates the nucleotide sequence of a DNA molecule according to the second aspect of the invention from Example 3;

FIG. 9 illustrates the amino acid sequence of a modified pro-α chain according to the first aspect of the invention from Example 3.

Figure 1:
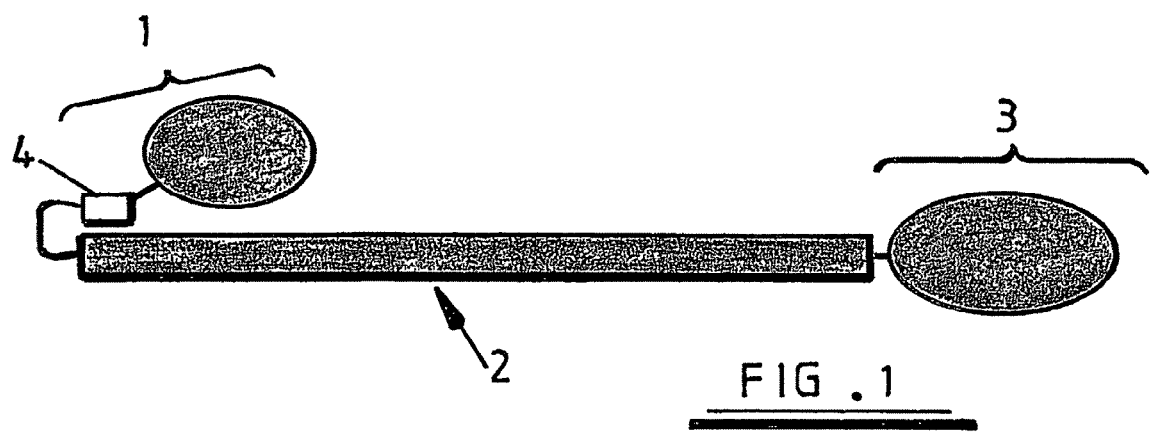
Figure 2:
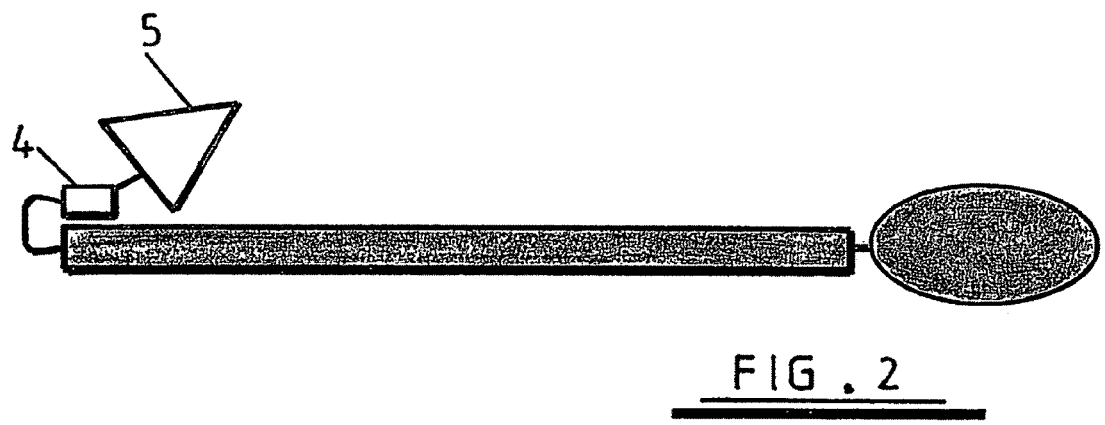

FIG. 1 illustrates a natural procollagen with an N-terminal propeptide 1, alpha helical domain 2 and a C-terminal propeptide 3. A procollagen N-Proteinase cleavage site 4 in the hinge region of the molecule (between 1 and 2) is also illustrated. FIG. 2 illustrates lam-proα1(III) or Lam-Coll™ a procollagen molecule according to the third aspect of the invention in which the N propeptide 1 has been replaced by at least one globular binding domain of laminin 5.

EXAMPLE 1

Design and Construction of a DNA molecule according to the second aspect of the invention, the Amino Acid sequence of the modified pro-α chain expressed therefrom according to a first aspect of the invention and the expression and characterization of modified procollagens prepared therefrom according to a third aspect of the invention.

A DNA molecule according to the second aspect of the invention was constructed comprising the entire coding region for the G1, G2 and G3 domains of the α-3 chain of Laminin 5 in place of the globular domain of the N-propeptide of the proα1(III) chain.

The cloning strategy for production of the DNA molecule involved the following primary PCR reactions.
1. Substrate: pRMI containing the complete cDNA for pro-α1 (III) chain of collagen (publicly available X 14420).

```
Oligonucleotides:
T3 (5' end)
5' AATTAACCCTCACTAAAGGG 3'        (SEQ ID NO:1)

SSG1-20R
(3' end)
5' ACAGAGATGTTGCCAAAATAATAGTGGGATG 3'  (SEQ ID NO:2)
```

Product A: 300 bp.

2. Substrate: Lam5α3-pSECTAG2C containing gene for α3 chain cloned in on Asp718I site

```
Oligonucleotides:
SSG1-20F (5' end)
                                  (SEQ ID NO:3)
5' TATTTTGGCAACATCTCTGTCCTTGTTTCTC 3'

LG3-20R (3' end)
                                  (SEQ ID NO:4)
5' CTTGACCATTAGCATCTTGCCACACCTTCAC 3'
```

Product B: 1800 bp

3. Substrate: pRM1

```
Oligonucleotides:
LG3-20F (5'end)
                                  (SEQ ID NO:5)
5' GCAAGATGCTAATGGTCAAGGACCTCAAGGC 3'

III-JL11 (3' end)
                                  (SEQ ID NO:6)
5' AGACCCTGCAGGTCCAACTT 3'
```

Product C: 700 bp.

The following secondary PCR Reactions were then carried out.
1) Substrate: Mixture of A (300 bp) and (B (1.8 kb) products
   Oligonucleotides: T3 (5'end)
      LG3-20R (3'end)
   Product AB: 2.1 kb
2) Substrate: Mixture of B (1.8 kb) and C(700 bp)
   Oligonucleotides: SSG1-20F (5'end)
      III-JL11 (3'end)
   Product BC: 2.5 kb Cloning of AB and BC Products into pBluescript Product AB was digested with HindIII and NotI and then ligated into pBS also digested with HindIII and NotI to generate G123AB-pBS plasmid. Product BC was digested with HindIII and BAMH1 and then ligated into pBS also digested with HindIII and BAMH1 to generate G123BC-pBS plasmid.

Generation of Chimeric LamG123-Collagen Gene

The G123AB-pBS plasmid was digested with NotI and HindIII and the 1.27 kb fragment was gel purified. The G123BC-pBS plasmid was digested with BamHI and HindIII and the 1.36 kb fragment was gel purified. The pRMI plasmid was digested with NotI and BamHI and the 6.8 kb fragment was gel purified.

The three fragments were ligated together to generate the gene encoding the LamG123-collagen fusion protein. Correct assembly of the lamG123-collagen gene was determined by DNA sequencing.

Modification of the LamG123-Collagen/pBluescript Plasmid

A NotI site was introduced 3' to the collagen sequence by standard PCR mediated site-directed mutagenesis using the oligonucleotides TAS14NotA and Oligo32merTAS12NotS, details of which are as follows:—

```
TAS14NotA (antisense)
                                  (SEQ ID NO:7)
5' GTTGTAANACGGCGGCCGCTGAATTGTAATAC 3'

Oligo32merTAS12NotS (sense)
                                  (SEQ ID NO:8)
5' GTATTACAATTCAGCGGCCGCCGTTTTACAAC 3'
```

The oligonucleotides introduce a NotI site within the pBluescript sequence about 50 bp downstream of the KpnI site.

Subcloning into pCEP4

The LamG123-collagen/pBluescript plasmid was digested with NotI to give a 6 kb fragment, which was ligated into NotI digested & phosphatased pCEP4 (10.4 kb). pCep4 vector (Invitrogen Life Technologies) is commercially available and the sequence may be found at http://www.invitrogen.com. Correct orientation of the 6 kb NotI fragment into pCep4 was determined by DNA sequencing.

Using the cloning strategy outlined above the procollagen type III N-propeptide Sequence prior to N100 was replaced with the sequence for the G123 domains of the α3 chain of Laminin-5, whilst retaining the collagen III signal sequence. The entire nucleotide sequence of the DNA molecule is presented in FIG. 3 (and SEQ ID NO: 9). FIG. 4 (and SEQ ID NO: 10) represents the amino acid sequence of the modified pro-α chain (a molecule according to the first aspect of the invention) which may be expressed from the DNA molecule. The junction between the G123 of laminin and procollagen sequences is shown as underlined in FIGS. 3 and 4.

The DNA molecule sub-cloned into the expression vector PCEP4 was expressed in HEK293-EBNA cells (Invitrogen Life Technologies).

HEK293-EBNA cells are known to those skilled in the art and details are available from http://www.invitrogen.com/Content/Tech-Online/molecular_biology/manuals_pps/293ebna_man.pdf HEK293-EBNA cells do not secrete procollagens and so are ideal for a negative background to express collagens in. Importantly, these cells do contain prolyl 4-hydroxylase which is vital for the hydroxylation of proline residues in the procollagen sequence and hence for the stability of the triple helix. The HEK293-EBNA line also expresses the EBNA-1 antigen that ensures that any plasmid DNA transfected into the cell is maintained episomally when the presence of that plasmid is selected for by the appropriate antibiotic (generally hygromycin).

Modified pro-α chains according to the first aspect of the invention are generated in the endoplasmic reticulum of the HEK293-EBNA cells. These molecules then automatically form a homotrimer (modified procollagen molecules according to the third aspect of the invention). The modified procollagen molecule produced from said cells is hereinafter referred to LamG123-coll.

A Integra CL 350 flask was seeded with HEK293-EPNA cells transformed with the DNA molecule and left for 7 days. The enriched medium was then harvested three times weekly (days 7, 9, 12, 14 and 16 after seeding).

Figure 5:
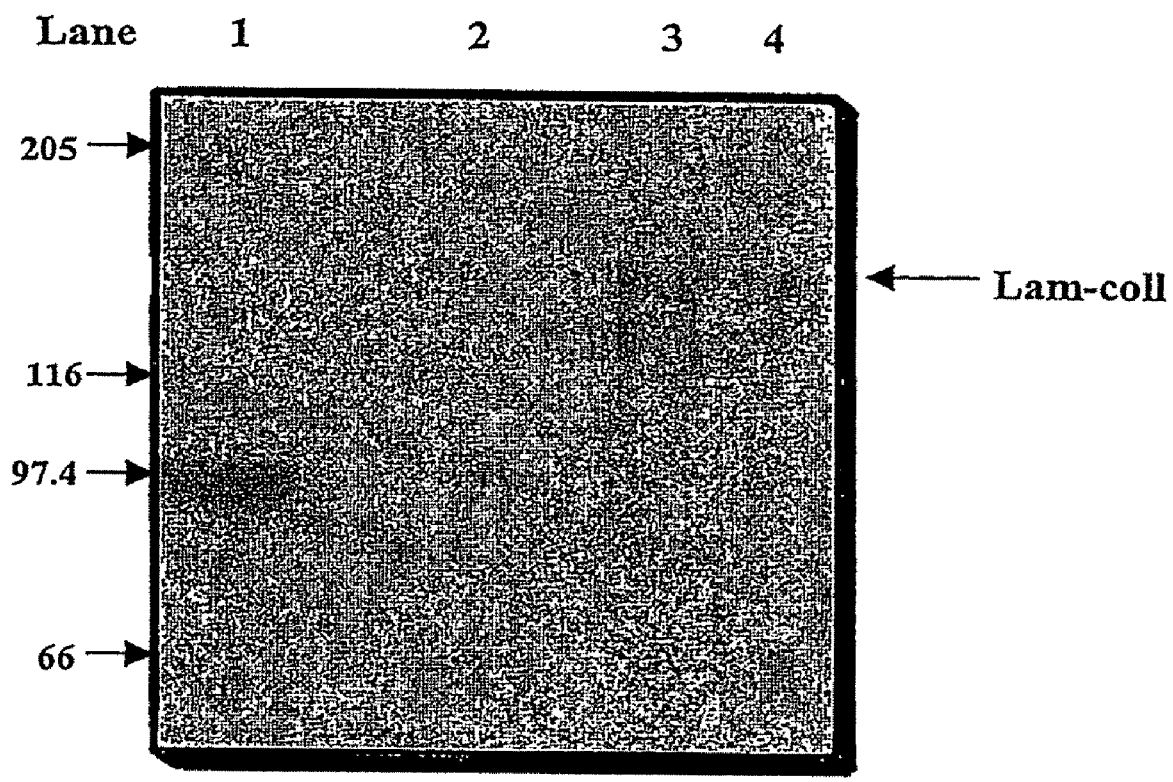
FIG. 5 is a photograph of a Western blot referred to in Examples 1 and 2.

LamG123-coll was characterised by Western blotting using an anti-collagen antibody. The results are presented in FIG. 5 of the accompanying drawings wherein Lane 1 is type III procollagen control, Lane 2 has medium from untransfected 293 cells, Lane 3 has medium from 293 EBNA cells transfected with LG123-coll and Lane 4 has medium from 293 EBNA cells transfected with LamG3-coll (see Example 2 below).

EXAMPLE 2

Design and Construction of a DNA molecule according to the second aspect of the invention, the Amino Acid sequence of the modified pro-α chain expressed therefrom according to a first aspect of the invention and the expression and characterization of modified procollagens prepared therefrom according to a third aspect of the invention.

A DNA molecule according to the second aspect of the invention was constructed comprising the coding region for the G3 domain of the α-3 chain of Laminin 5 in place of the globular domain of the N-propeptide of the proα1(III) chain.

The cloning strategy for production of the DNA molecule involved the following primary PCR reactions.
1. Substrate pRMI containing the complete cDNA for pro-α1 (III) chain of collagen (publicly available X 14420).

```
Oligonucleotides:
T3 (5' end)
                                          (SEQ ID NO:1)
5' AATTAACCCTCACTAAAGGG 3'

SSLAMG3-2 (3'end)
                                         (SEQ ID NO:11)
5' GCTTCCAGTCTTCCGAGCATGCCAAAATAATAGTGGG 3'
```

Product A: 300 bp.
2. Substrate: Lam5α3-pSECTAG2C containing gene for α3 chain cloned in on Asp718I site

```
Oligonucleotides:
SLAMG3-1 (5'end)
                                         (SEQ ID NO:12)
5' CCCACTATTATTTTGGCATGCTCGGAAGACTGGAAGC 3'

LG3-20R (3' end)
                                          (SEQ ID NO:4)
5' CTTGACCATTAGCATCTTGCCACACCTTCAC 3'
```

Product B: 700 bp

The following secondary PCR Reaction was then carried out.
1) Substrate: Mixture of A (300 bp) and B (700 bp) products
   Oligonucleotides: T3 (5'end)
       LG3-20R (3'end)
   Product AB: 1.0 kb Cloning of AB Product into pBluescript Product AB was digested with HindIII and NotI and then ligated into pBS also digested with HindIII and NotI to generate G3AB-pBS plasmid.

Generation of Chimeric LamG-Collagen Gene

The G3AB-pBS plasmid was digested with NotI and HindIII and the 200 bp fragment was gel purified. The G3AB-pBS plasmid was digested with BamHI and HindIII and the 1.36 kb fragment was gel purified. The pRMI plasmid was digested with NotI and BamHI and the 6.8 kb fragment was gel purified.

The three fragments were ligated together to generate the gene encoding the LamG3-collagen fusion protein. Correct assembly of the lamG3-collagen gene was determined by DNA sequencing.

Modification of the LamG3-Collagen/pBluescript Plasmid

A NotI site was introduced 3' to the collagen sequence by standard PCR mediated site-directed mutagenesis using the oligonucleotides TAS14NotA and Oligo32merTAS12NotS, (see Example 1 above)

The oligonucleotides introduce a NotI site within the pBluescript sequence about 50 bp downstream of the KpnI site.

Subcloning into pCEP4

The LamG3-collagen/pBluescript plasmid was digested with NotI to give a 5 kb fragment, which was ligated into NotI digested & phosphatased pCEP4 (10.4 kb). Correct orientation of the 5 kb NotI fragment into pCep4 was determined by DNA sequencing.

Using the cloning strategy outlined above the procollagen type III N-propeptide Sequence prior to N100 was replaced with the sequence for the G3 domain of the α3 chain of Laminin-5, whilst retaining the collagen III signal sequence. The entire nucleotide sequence of the DNA molecule is presented in FIG. 6 (and SEQ ID NO: 13). FIG. 7 (and SEQ ID NO: 14) represents the amino acid sequence of the modified pro-α chain (a molecule according to the first aspect of the invention) which may be expressed from the DNA molecule. The junction between the G3 of laminin and procollagen sequences is shown as underlined in FIGS. 6 and 7.

The DNA molecule sub-cloned into the expression vector PCEP4 was expressed in HEK293-EBNA cells (Invitrogen Life Technologies).

Modified pro-α chains according to the first aspect of the invention are generated in the endoplasmic reticulum of the HEK293-EBNA cells. These molecules then automatically form a homotimer (modified procollagen molecules according to the third aspect of the invention). The modified procollagen molecule produced from said cells is hereinafter referred to LamG3-coll.

A Integra CL 350 flask was seeded with HEK293-EPNA cells transformed with the DNA molecule from this Example and left for 7 days. The enriched medium was then harvested three times weekly (days 7, 9, 12, 14 and 16 after seeding).

LamG3-coll was characterised by Western blotting using an anti-collagen antibody. The results are presented in FIG. 5 wherein Lane 4 has medium from 293 EBNA cells transfected with LamG3-coll.

EXAMPLE 3

Design and Construction of a DNA molecule according to the second aspect of the invention, the Amino Acid sequence of the modified pro-α chain expressed therefrom according to a first aspect of the invention and the expression and characterization of modified procollagens prepared therefrom according to a third aspect of the invention.

A DNA molecule according to the second aspect of the invention was constricted comprising the entire coding region for secretory leukocyte protease inhibitor precursor ("SLPI") in place of the globular domain of the N-propeptide of the proα1(III) chain. "SLPI-Collagen" (or slpi-coll) was produced by constructing the SLPICollagenIII/pCEP4 construct, involving polymerase chain reactions, restriction digestion and ligation.

Polymerase Chain Reactions

The Platinum® Pfx DNA polymerase (Invitrogen, U.K.), the corresponding recipe and cycling programme as recommended by the manufacturer were used for all the PCRs carried out in cloning SLPI-Collagen. Three rounds of PCR were required for the assembly of SLPI-CollagenIII/pCEP4 construct.

In the first round, the sequence encoding human SLPI was amplified from the image clone 4733996 (UK Human Genome Mapping Project Resource Centre, U.K.). The following primers were employed in the PCR:

```
5' primer
                                          (SEQ ID NO:15)
5'-CTTGTAGATGCGGCCGCatgaagtccagcggcctctt-3'

3' primer
                                          (SEQ ID NO:16)
5'-cttcaacagcagctttcacaggggaaacgc-3'
```

The primers resulted in the SLPI PCR products containing a Not I restriction site (GCGGCCGC) at the 5' end, indicated by bold capital letters in the sequence above, and at its 3' end, there were 10 base pairs encoding the 5' end of human type III collagen, indicated by italic small letter in the sequence above. The annealing temperature was 48° C. The PCR product was expected to have a size of 0.42 kilo basepairs (kbp). It was then gel purified using Qiagen Gel Extraction Kit (Qiagen, U.K.).

In the second round of PCR, part of the sequences encoding human type III collagen was amplified from the construct pRMI using the following primers:

```
5' primer
                                          (SEQ ID NO:17)
5'-tgtgaaagctgctgttgaaggaggatgttc-3'

3' primer
                                          (SEQ ID NO:18)
5'-ggacctggtcgaccactttc-3'
```

The italic small letters indicate nucleotides encoding SLPI. The annealing temperature was 50° C. pRMI is a pBluescript SK (−) vector carrying a human type III collagen insert. As a result, the 5' end of the PCR product had 10 base pairs encoding the 3' end of SLPI. The expected size of the Collagen III PCR product was 1.603 kbp. It was then gel purified using Qiagen Gel Extraction Kit (Qiagen).

In the third round of PCR, the sequences encoding SLPI-Collagen III fragment were amplified from the purified SLPI and Collagen III PCR products. The following primers were used:

```
5' primer
                                          (SEQ ID NO:17)
5'-tgtgaaagctgctgttgaaggaggatgttc-3'

3' primer
                                          (SEQ ID NO:18)
5'-ggacctggtcgaccactttc-3'
```

The resulting PCR product was expected to have a size of 2.023 kbp. It also contained a Not I and a Xma I restriction sites. It was then gel purified by the Qiagen gel extraction kit.

Restriction, Digestion and Ligation.

The purified SLPI-Collagen III PCR product was digested with restriction enzymes (Roche, U.K.) Not I and Xma I while the vector pRMI was digested with Not I and EcoR V followed by Xma I. The digests were then gel purified by the Qiagen gel extraction kit and this was followed by the dephosphorylation of the vector digest with alkaline phosphatase. Upon assessing the yield of the inserts and the dephosphorylated vector, a ligation reaction was set up using high concentration T4 DNA ligase (New Englands Biolabs, U.K.), according to manufacturer's instruction.

Transformation and Colony Screening.

5 μl of the ligation reaction was transformed into the chemically competent DH5α cells. The DNA from each colony was extracted by Qiagen miniprep kit (Qiagen). A positive clone was distinguished by restriction digestion with Xho I, yielding fragments of the right sizes on the agarose gel (1.936, 2.520 and 4.680 kbp).

Sequencing of the PCR Product.

Once a positive clone was identified, sequencing reactions were carried out to ensure that no error was introduced into the PCR product by the polymerase. The primers used in the sequencing reaction are shown below:

```
SK-T7
5'-gta ata cga ctc act ata ggg c-3'   (SEQ ID NO:19)

C3For1
5'-gct gtt gaa gga gga tgt-3'          (SEQ ID NO:20)

C3For2
5'-aga ggc ttc gat gga cga-3'          (SEQ ID NO:21)

C3For3
5'gga ctg cga ggt ggt gca-3'           (SEQ ID NO:22)

C3Rev1
5'-ttc tcc cag gaa tac cag-3'          (SEQ ID NO:23)

C3Rev2
5'-agg gaa tcc ggc agt tcc-3'          (SEQ ID NO:24)

C3Rev3
5'-ctc ggg gac cag atg gcc-3'          (SEQ ID NO:25)
```

Subcloning of SLPI-Collagen III PCR Product into pCEP4.

In order to subclone SLPI-Collagen III into pCEP4, SLPI-Collagen III/SK (+) was digested with Not I. This was followed by filling ends with Klenow (Roche) and restriction digestion with Hind III. The same procedures were performed on the vector pCEP4 except Not I was substituted by Kpn I. The insert and vector were then gel purified using the Qiagen gel extraction kit (Qiagen). In order to prevent self-ligation, the vector was also dephosphorylated with alkaline phosphatase (Roche).

A ligation reaction using high concentration T4 DNA ligase (NEB) was set up after the yields of the insert and vector were assessed. Chemically competent DH5α cells were then transformed with the construct. The DNA from each colony was extracted with Qiagen miniprep kit (Qiagen). Upon digestion with Xho I, a positive clone was revealed by the sizes of the DNA fragments obtained (1.924, 2.520 and 11.480 kbp).

Using the cloning strategy outlined above the procollagen type III N-propeptide sequence was replaced with the sequence for SLPI whilst retaining the collagen III signal sequence. The entire nucleotide sequence of the DNA molecule is presented in FIG. 8 (and SEQ ID NO: 26). FIG. 9 (and SEQ ID NO: 27) represents the amino acid sequence of the modified pro-α chain (a molecule according to the first aspect of the invention) which may be expressed from the DNA molecule. The underlined sections in FIGS. 8 and 9 relate to the DNA and amino acid sequence of SLPI respectively, whilst the non-underlined sections refer to DNA and amino acid sequences for human procollagen III starting from the von Willebrand Factor.

Figure 10:
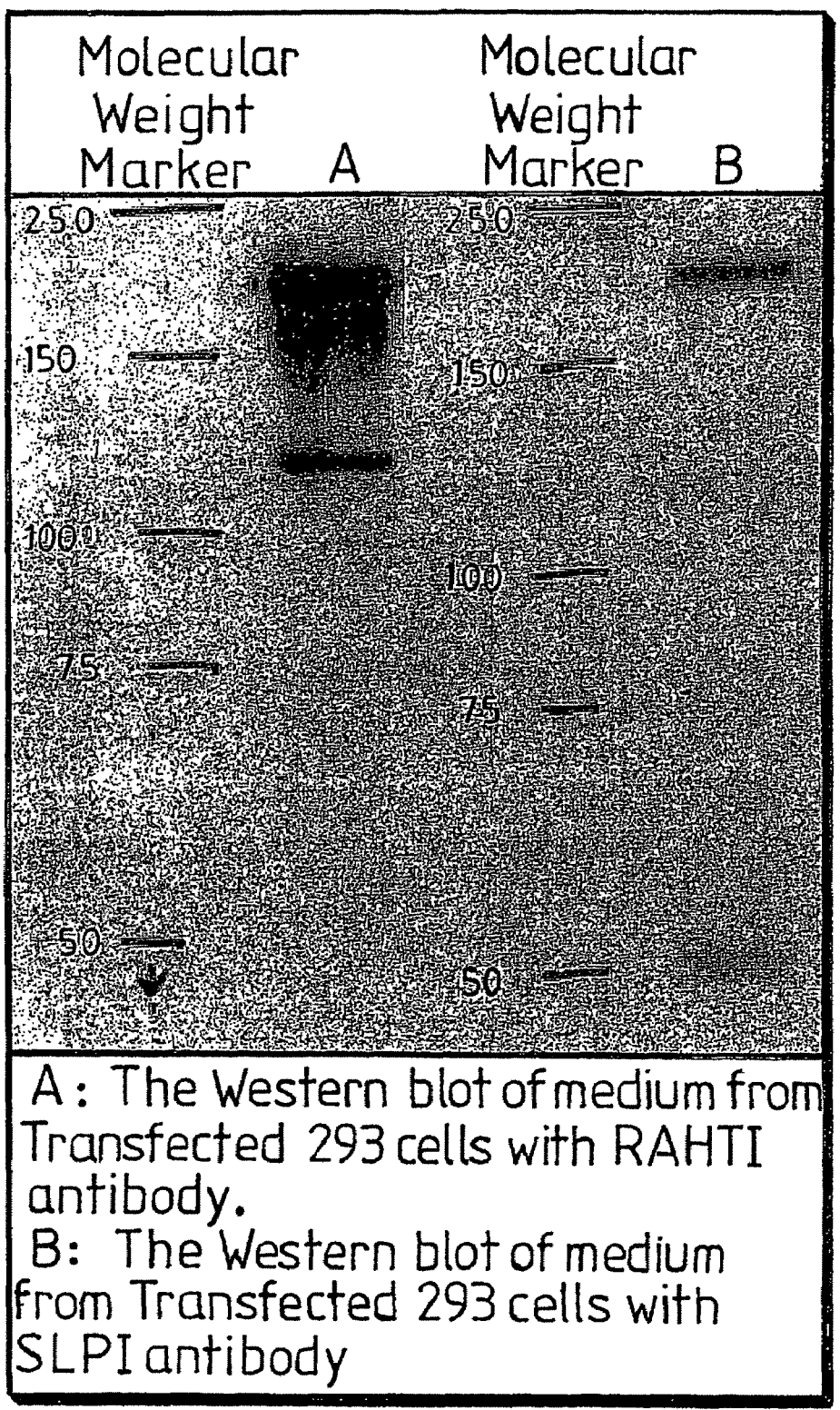
FIG. 10 is a photograph of a Western Blot referred to in Example 3.

The DNA molecule cloned into the pCEP4 vector was expressed in HEK 293 Ebna cells, see FIG. 10. The band for slpi-col is the single band in the western blotted into anti-slpi antibody.

The above Examples illustrate that modified collagens may be produced that contain part or all of a laminin or SLPI molecule. These modified domains are able to impart specific desirable functional characteristics to the collagen to enhance the wound healing properties of the molecule.

The invention claimed is:

1. A method of treating a wound or fibrotic disorder comprising administering to a subject in need of such treatment a therapeutically effective amount of a modified pro-α chain wherein the modified pro-α chain comprises at least part of a secretory leukocyte protease inhibitor wherein the at least part of a secretory leukocyte protease inhibitor is placed N-terminal to a triple helical forming domain of the pro-α chain.

2. The method of treating a wound or fibrotic disorder of claim 1 wherein the triple helical forming domain is from a fibrillar forming pro-α chain.

3. The method of treating a wound or fibrotic disorder of claim 1 wherein the triple helical forming domain is from a type I, II, III, V or XI pro-α chain.

4. The method of treating a wound or fibrotic disorder of claim 1 wherein the triple helical forming domain is from a pro-α (III) chain.

5. The method of treating a wound or fibrotic disorder of claim 1 wherein the modified pro-α chain further comprises a procollagen N-propeptide sequence, wherein the procollagen N-terminal sequence is replaced prior to N167 with the sequence for the secretory leukocyte protease inhibitor.

6. The method of treating a wound or fibrotic disorder of claim 5 wherein an N-proteinase cleavage site associated with the N-terminal propeptide domain is modified such as to alter the domain's susceptibility to cleavage.

7. The method of treating a wound or fibrotic disorder of claim 6 wherein the N-proteinase cleavage site is modified such that the domain may not be cleaved.

8. The method of treating a wound or fibrotic disorder of claim 1 wherein the pro-α chain comprises the entire secretory leukocyte protease inhibitor.

9. The method of treating a wound or fibrotic disorder of claim 1 wherein the modified pro-α chain further comprises a procollagen N-propeptide sequence, wherein the procollagen N-propeptide sequence is replaced prior to N167 within the sequence for the secretory leukocyte protease inhibitor.

10. The method of treating a wound or fibrotic disorder of claim 9 wherein an N-proteinase cleavage site associated with the N-terminal propeptide domain is modified such as to alter the domain's susceptibility to cleavage.

11. The method of treating a wound or fibrotic disorder of claim 10 wherein the N-proteinase cleavage site is modified such that the domain may not be cleaved.

12. The method of treating a wound or fibrotic disorder of claim 11 wherein a region between the triple helical forming domain and the N-propeptide forming domain of the pro-α chain is modified to confer resistance to N-proteinases.

13. The method of treating a wound or fibrotic disorder of claim 12 wherein Pro-Gln in the region is altered to Leu-Pro.

14. A method of treating a wound or fibrotic disorder comprising administering to a subject in need of such treatment a therapeutically effective amount of a procollagen molecule comprising a trimer of pro-α chains wherein the molecule comprises SEQ ID NO: 27.

15. A method of treating a wound or fibrotic disorder comprising administering to a subject in need of such treatment a therapeutically effective amount of a procollagen molecule comprising a trimer of pro-α chains characterized in that at least one of the pro-α chains is a modified pro-α chain comprising at least a part of a secretory leukocyte protease inhibitor wherein the at least part of a secretory leukocyte protease inhibitor is placed N-terminal to a triple helical forming domain of the pro-α chain.

16. The method of treating a wound or fibrotic disorder of claim 15, wherein the procollagen molecule is part of a collagen matrix.

17. The method of treating a wound or fibrotic disorder of claim 16, wherein the collagen matrix is part of a dressing.

18. The method of treating a wound or fibrotic disorder of claim 16, wherein the collagen matrix comprises collagen monomers having modified propeptide domains derived from the procollagen molecule wherein the pro-α chain of the procollagen molecule is truncated C-terminal to the triple helical forming domain.

19. A method of treating a wound or fibrotic disorder comprising administering to a subject in need of such treatment a therapeutically effective amount of a collagen polymer comprising at least one modified collagen monomer, wherein said modified collagen monomer comprises at least part of a secretory leukocyte protease inhibitor placed N-terminal to a triple helical forming domain in a collagen monomer.

* * * * *